(12) United States Patent
Zeugolis et al.

(10) Patent No.: US 10,619,133 B2
(45) Date of Patent: Apr. 14, 2020

(54) ENGINEERED LIVING TISSUE SUBSTITUTE

(75) Inventors: Dimitrios Zeugolis, Salthill (IE); Abhigyan Satyam, Newcastle (IE)

(73) Assignee: NATIONAL UNIVERSITY OF IRELAND, GALWAY, Galway (IE)

( * ) Notice: Subject to any disclaimer, the term of this patent is extended or adjusted under 35 U.S.C. 154(b) by 126 days.

(21) Appl. No.: 14/124,568

(22) PCT Filed: Jun. 8, 2012

(86) PCT No.: PCT/EP2012/060945
§ 371 (c)(1),
(2), (4) Date: Aug. 13, 2014

(87) PCT Pub. No.: WO2012/168465
PCT Pub. Date: Dec. 13, 2012

(65) Prior Publication Data
US 2015/0024424 A1 Jan. 22, 2015

(30) Foreign Application Priority Data

Jun. 8, 2011 (EP) .................................. 11169176

(51) Int. Cl.
C12N 5/073 (2010.01)
C12N 5/00 (2006.01)
C12N 5/077 (2010.01)
C12N 5/071 (2010.01)

(52) U.S. Cl.
CPC ......... *C12N 5/0605* (2013.01); *C12N 5/0018* (2013.01); *C12N 5/0656* (2013.01); *C12N 5/0688* (2013.01); *C12N 2500/34* (2013.01); *C12N 2500/38* (2013.01); *C12N 2500/50* (2013.01)

(58) Field of Classification Search
None
See application file for complete search history.

(56) References Cited

U.S. PATENT DOCUMENTS

| 2002/0028192 A1 | 3/2002 | Dimitrijevich et al. | |
|---|---|---|---|
| 2005/0089512 A1 | 4/2005 | Schlotmann et al. | |
| 2011/0244570 A1* | 10/2011 | Birk ..................... | C12N 5/0068 435/375 |

FOREIGN PATENT DOCUMENTS

| WO | WO 2006/097701 A2 | | 9/2006 | |
|---|---|---|---|---|
| WO | WO 2010/027789 | * | 3/2010 | ............... C12N 5/02 |
| WO | WO 2012168465 | * | 6/2011 | ............ C12N 5/0018 |

OTHER PUBLICATIONS

Chen et al., Advanced Drug Delivery Reviews 63 (2011) pp. 277-290.*
Lareu et al., Collagen matrix deposition is dramatically enhanced in vitro when crowded with charged macromolecules: The biological relevance of the excluded volume effect, FEBS Letters 581 (2007), pp. 2709-2714.*
Narayanan et al., Distribution of Receptors to Collagen and Globular Domains of C1q in Human Lung Fibroblasts, A,/ K/ Respir. Cell Mol. Biol. vol. 17, pp. 84-90.*
Ribeiro et al., Isolation of Human Umbilical Arterial Smooth Muscle Cells (HUASMC), Journal of Visualized Experiments 41, pp. 1-2.*
Mazlyzam et al., Human Serum is an Advantageous Supplement for Human Dermal Fibroblast Expansion: Clinical Implications for Tissue Engineering of Skin, Archives of Medical Research, vol. 39 (2008), pp. 743-752.*
Ahmed, M.R., et al., Microwave Irradiated Collagen Tubes as a Better Matrix for Peripheral Nerve Regeneration, Brain Research 1046(1-2):55-67, 2005.
Archibald, S., et al., Monkey Median Nerve Repaired by Nerve Graft or Collagen Nerve Guide Tube, J. Neurosci., Part 2, 15(5):4109-4123, 1995.
Chen, C., et al., Applying Macromolecular Crowding to Enhance Extracellular Matrix Deposition and Its Remodeling In Vitro for Tissue Engineering and Cell-Based Therapies, Advanced Drug Delivery Reviews 63(4-5_:277-290, Apr. 1, 2011.
Chen, H.-M., et al., λ-Carrageenan Oligosaccharides Elicit Reactive Oxygen Species Production Resulting in Mitochondrial-Dependent Apoptosis in Human Umbilical Vein Endothelial Cells, International Journal of Molecular Medicine 24(6):801-806, Dec. 2009.
Chen, P.-R., et al., Biocompatibility of NGF-Grafted GTG Membranes for Peripheral Nerve Repair Using Cultured Schwann Cells, Biomaterials 25(25):5667-5673, 2004.
Chen, Y.-S., et al., An In Vivo Evaluation of a Biodegradable Genipin-Cross-Linked Gelatin Peripheral Nerve Guide Conduit Material, Biomaterials 26(18):3911-3918, 2005.
Chew, S.Y., et al., Aligned Protein-Polymer Composite Fibers Enhance Nerve Regeneration: A Potential Tissue-Engineering Platform, Adv. Funct. Mater. 17(8): p. 1288-1296, 2007.
Colin, W., and R. Donoff, Nerve Regeneration Through Collagen Tubes, J. Dent. Res. 63(7):987-993, 1984.
Den Dunnen, W., et al., A New PLLA/PCL Copolymerfor Nerve Regeneration, J. Mater. Sci.: Mater. Med. 4:521-525, 1993.
Evans, G., et al., In Vivo Evaluation of Poly(L-Lactic Acid) Porous Conduits for Peripheral Nerve Regeneration, Biomaterials 20(12):1109-1115, 1999.
Evans, G.R., et al., Bioactive Poly(L-Lactic Acid) Conduits Seeded With Schwann Cells for Peripheral Nerve Regeneration, Biomaterials 23(3):841-8, 2002.
Evans, P., et al., Cold Preserved Nerve Allografts: Changes in Basement Mmembrane, Viability, Immunogenicity, and Regeneration, Muscle Nerve 21(11):1507-1522, 1998.
Harley, B.A., et al., Fabricating Tubular Scaffolds With a Radial Pore Size Gradient by a Spinning Technique, Biomaterials 27(6):866-874, 2006.

(Continued)

*Primary Examiner* — Scott Long
*Assistant Examiner* — Evelyn Y Pyla
(74) *Attorney, Agent, or Firm* — Knobbe, Martens, Olson & Bear LLP

(57) ABSTRACT

The present invention relates generally to the field of tissue engineering and in particular to the production of tissue films or cell matrices, which can be used as a living tissue substitute or an artificial tissue construct in tissue repair or replacement.

10 Claims, 19 Drawing Sheets

(56) References Cited

OTHER PUBLICATIONS

Harve, K., et al., Macromolecular Crowding in vitro as Means of Emulating Cellular Interiors: When Less Might Be More, PNAS 105(51):119, 2008.

Itoh, S., et al., Evaluation of Cross-Linking Procedures of Collagen Tubes Used in Peripheral Nerve Repair, Biomaterials 23(23):4475-4481, 2002.

Ju, Y.-E., et al., Enhanced Neurite Growth from Mammalian Neurons in Three-Dimensional Salmon Fibrin Gels, Biomaterials 28(12):2097-2108, 2007.

Kim, Y.-T., et al., The Role of Aligned Polymerfiber-Based Constructs in the Bridging of Long Peripheral Nerve Gaps, Biomaterials 29:3117-3127, 2008.

Lareu, R., et al., Emulating a Crowded Intracellular Environment In Vitro Dramatically Improves RT-PCR Performance, Biochem. Biophys. Res. Commun. 363(1):171-177, 2007.

Lareu, R.R., et al., Collagen Matrix Deposition Is Dramatically Enhanced In Vitro When Crowded With Charged Macromolecules: The Biological Relevance of the Excluded Volume Effect, FEBS Letters 581:2709-2714, 2007.

Lareu, R.R., et al., In Vitro Enhancement of Collagen Matrix Formation and Crosslinking for Applications in Tissue Engineering: A Preliminary Study, Tissue Engineering 13(2):385-391, Feb. 1, 2007.

Li, X.-K., et al., Characteristics of PLGA-Gelatin Complex as Potential Artificial Nerve Scaffold, Colloids and Surfaces B: Biointerfaces 57(2):198-203, 2007.

Madison, R., et al., Increased Rate of Peripheral Nerve Regeneration Using Bioresorbable Nerve Guides and a Laminin-Containing Gel, Exp. Neurol. 88(3):767-772, 1985.

Munishkina, L.A., et al., Guiding Protein Aggregation With Macromolecular Crowding, Biochemistry, 47(34):8993-9006, Aug. 26, 2008.

Pereira, R.C., Novel Injectable Gel (System) As a Vehicle for Human Articular Chondrocytes in Cartilage Tissue Regeneration, Journal of Tissue Engineering and Regenerative Medicine 3(2):97-106, Feb. 1, 2009.

Shah, D., et al., Effects of Polydisperse Crowders on Aggregation Reactions: A Molecular Thermodynamic Analysis, Journal of Chemical Physics 134(6), Feb. 9, 2011, 7 pages.

Van Den Berg, B., et al., Effects of Macromolecular Crowding on Protein Folding and Aggregation, The EMBO Journal 18(24):6927-6933, 1999.

Willerth, S.M., and S.E. Sakiyama-Elbert, Approaches to Neural Tissue Engineering Using Scaffolds for Drug Delivery, Advanced Drug Delivery Reviews 59(4-5):325-338, 2007.

Zimmerman, S.B., and B. Harrison, Macromolecular Crowding Increases Binding of DNA Polymerase to DNA: An Adaptive Effect, Proc. Natl. Acad. Sci. USA, 84:1871-1875, Apr. 1987.

Zhou, Z., et al., Crowded Cell-Like Environment Accelerates the Nucleation Step of Amyloidogenic Protein Misfolding, The Journal of Biological Chemistry 284(44):30148-30158, Oct. 30, 2009.

* cited by examiner

WI-38 Fibroblasts, DxS(500kD)-100μg/mL, FBS concentrations in %

WS-1 Fibroblasts, DxS(500kD)-100μg/mL, FBS concentrations in %

FIG. 11A
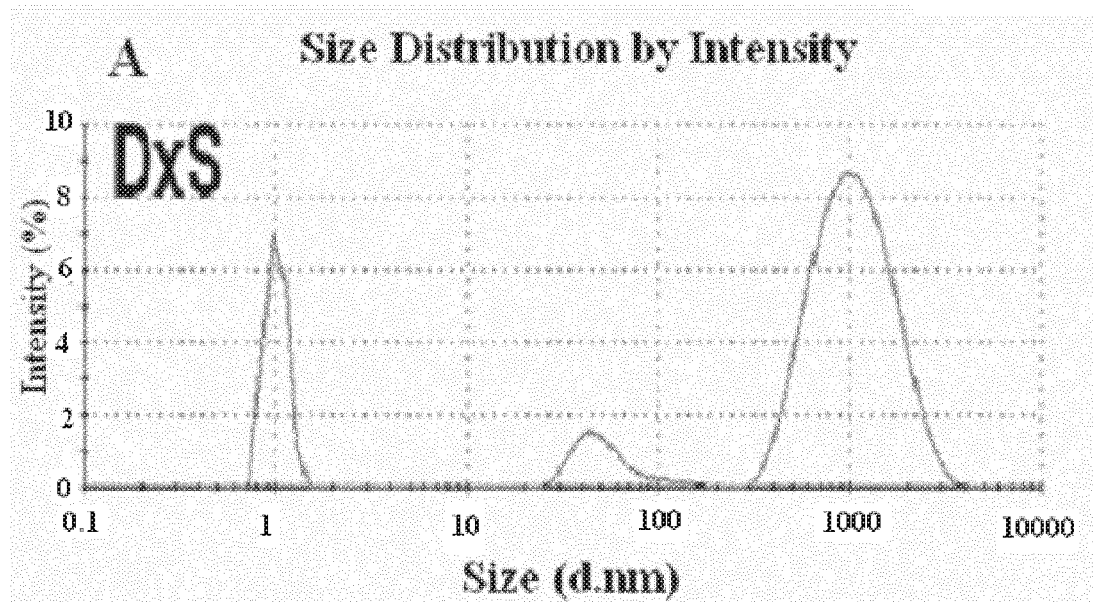
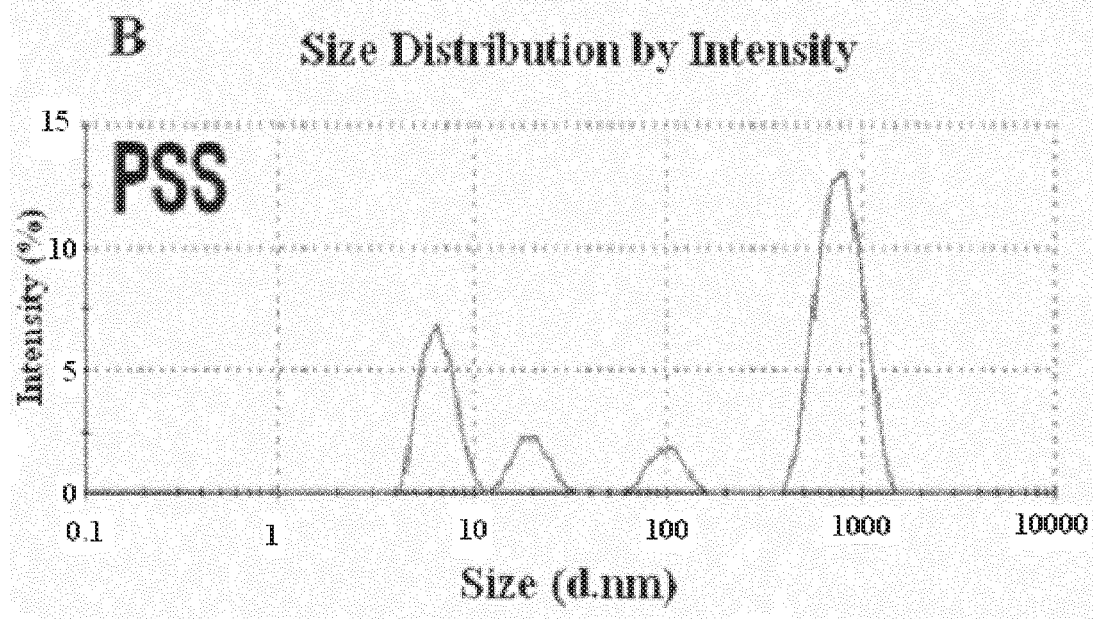
FIG. 11B

FIG. 15C
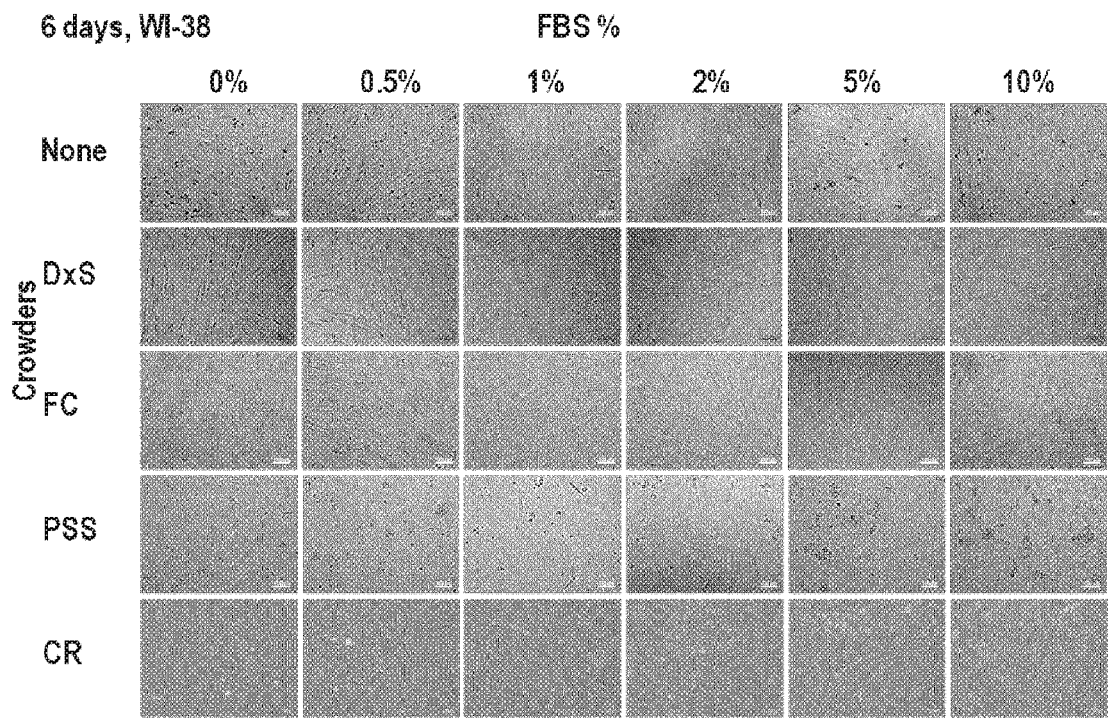
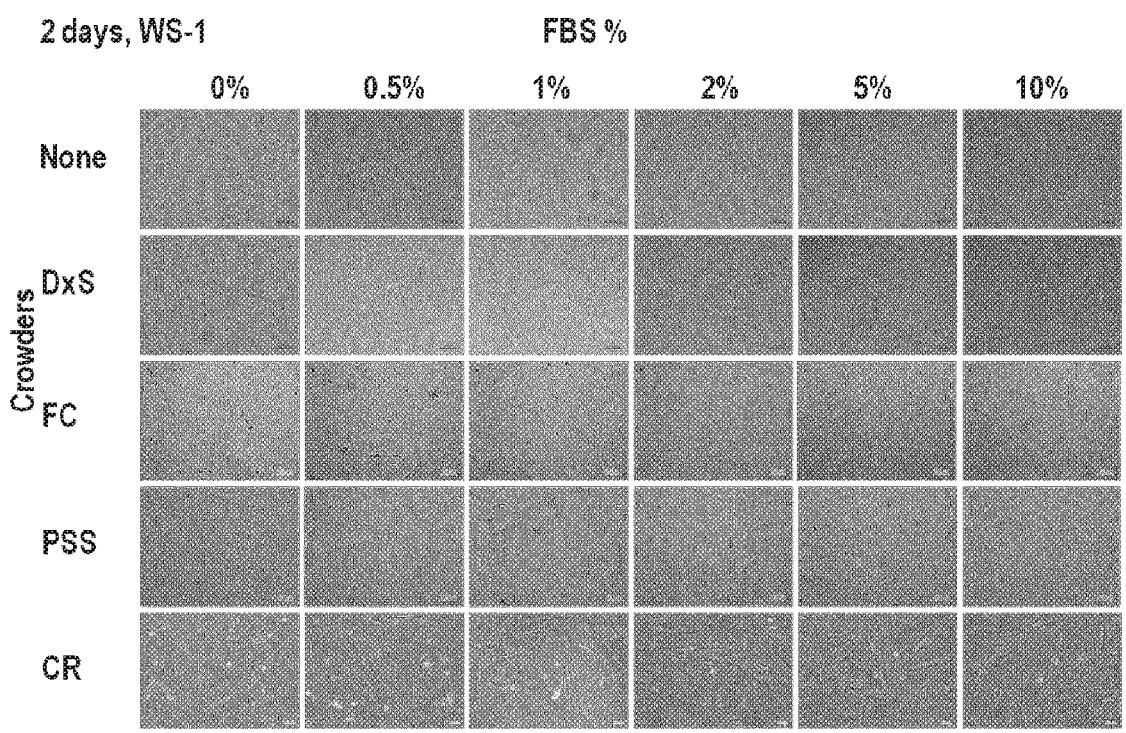
FIG. 15D

ENGINEERED LIVING TISSUE SUBSTITUTE

FIELD OF THE INVENTION

The present invention relates generally to the field of tissue engineering and in particular to the production of tissue films, sheets or cell matrices, which can be used as a living tissue substitute or an artificial tissue construct in tissue repair or replacement.

BACKGROUND TO THE INVENTION

The goal of tissue engineering is to repair or replace tissues and organs with artificial tissue constructs. Scaffolds are typically used for this process, giving mechanical support, and assisting in cell migration and attachment, cell retention and delivery at the site of repair. The scaffold thus mimics the natural matrix found in the body. In other situations, films or layers of tissue itself may be suitable for the repair or transplant. The cells in such films should thus be as similar as possible to those produced naturally by the body. It is thus important that cells grown into these tissue layers or films are properly aligned, and metabolise to produce factors that the tissue they are destined to replace would produce.

The extracellular matrix is a complex variety of glycoproteins and proteoglycans, which provides tissue integrity, acts as a native scaffold for cell attachment and interaction and acts as a reservoir for growth factors. For most connective tissues, collagen makes up the bulk of the extracellular matrix, where it functions as a structural protein as well as a binding partner for glycans that store growth factors.

Collagen is a family of extracellular matrix proteins, the most abundant being type I found in skin, tendon, bone, corneal, type IV found in all basement membranes and type VII found in the basement membrane of skin, oral mucosa and cornea. These collagen assemblies differ depending on the tissue location and function.

The deposition of a collagen matrix depends on the conversion of denovo synthesised pro-collagen to collagen in the extracellular space immediately before its release into the space. This limiting step for collagen matrix deposition is very slow in vitro, both in monolayer cultures and in three dimensional scaffolds.

For a number of tissue engineering applications, tissue grafts (autografts, allografts or xenografts) are considered to be the 'gold standards'. However, the limited supply of autografts and certain donor site morbidity restricts their utilisation. The use of allografts and xenografts has also been questioned due to poor success rates, possibilities of immune rejection and potential transmission of disease. To this end, tissue engineering was pioneered as the only viable alternative to the transplantation crisis. Several degradable and non-degradable synthetic materials have been evaluated over the years [2-10]. However, non-degradable synthetic materials may become harmful due to mechanical impingement or infection and require a second operation, whilst the degradation products of biodegradable synthetic materials could be deleterious to the surrounding cells and tissues. Natural biomaterials such as collagen [15-18], gelatin [19, 20] and fibrin [21] have been used as raw materials for scaffold fabrication with promising early results. In particular, the use of collagen as a raw material for scaffold fabrication has been advocated because, as a natural occurring biopolymer that constitutes approximately one third of the total body proteins, it is perceived by the body as a normal constituent rather than foreign matter. Despite advancements in purification methods and analytical assays that have assured low immunogenicity and antigenicity, collagen remains an animal derived by-product and its use in clinical applications can be limited due to concerns of inter-species transmission of disease, especially for collagen extracted from bovine tissues (e.g. Bovine Spongiform Encephalopathy and Creutzfeldt Jakob Disease). In fact, 2-3% of patients have an immune response to collagen implants using collagen derived from land-based animals. For this reason, human recombinant collagen has been investigated for scaffold fabrication. Although several expression systems have successfully produced human recombinant procollagens, in all cases procollagen expression levels have been low (15 mg/ml for mammalian cell culture; 15 mg/ml in yeast; and 60 mg/ml in baculovirus) which was prohibited commercialisation and clinical applications. Moreover, whilst recombinant collagens can be expressed in a thermo-stable triple helical form, they lack specific domains otherwise present in native fibrillar collagens, which can compromise their biological function and further reduce their use. In light of this, it has been predicted that companies developing new implantable products are more likely to focus on human collagen products, rather than on products utilising animal-sourced collagen.

Indeed, advancements in molecular and cell biology have allowed the use of cell-based therapies for tissue engineering and regenerative medicine applications. The concept is that replacement, repair and restoration of function can be accomplished best using cells that will create their own host-specific extracellular matrix. Indeed, cells are professional matrix makers and assemble into large aggregates together with ligands, growth factors and other matrix components with a precision and stoichiometric efficiency that is still unmatched by man-made devices, recombinant technology-derived components or chemical compounds. Cell-based injectable systems and cell-sheets derived from autologous primary cell isolates; from established cell lines; and from a variety of stem cells have been used for numerous clinical targets, including cornea, skin, blood vessel, cartilage, lung, cardiac patch, oesophagus and periodontal applications.

Cultured cells deposit extracellular matrix (ECM) molecules and form cell-to-cell junctions. However, typical proteolytic harvest (by trypsin) digests both deposited ECM and cell-to-cell junctions. In contrast, culture dishes covered with a temperature-responsive polymer allow harvesting of intact cell sheets along with their deposited ECM, by simple temperature reduction. Despite the success of cell sheet tissue engineering in regenerative medicine, this technology has still not taken off primarily due to the substantial long period of time required to culture the cells and develop an implantable cell-sheet.

Herein, for first time, we describe the production of cell-sheets within 24-48 h from human cells using a biophysical approach that governs the intra- and extra-cellular milieu in multicellular organisms, termed macromolecular crowding, that invites cells to create their own matrices. The principal that the approach is based on is that the deposition of a collagen matrix depends on the conversion of de novo synthesised procollagen to collagen in the crowded extracellular space or immediately before its release into the same. The rate limiting step of collagen I deposition is the proteolytic conversion of procollagen to collagen. This step is catalysed by procollagen C-proteinase and proteolytic modification of its allosteric regulator. In vivo, the extracellular space is highly crowded (FIG. 1); even dilute body fluids are highly crowded: blood contains 80 g/l protein;

urine contains 36-50 g/l solids, and the conversion of procollagen to collagen takes place very fast (FIG. 2). However, in vitro cells are grown in highly dilute conditions; this, in the human body, would represent a medical pathology. However, this situation can be remedied, by adding macromolecules of defined hydrodynamic radius to culture media and thus creating excluded volume effects with defined volume fraction occupancies. Conventional cell culture systems are far from crowded environments (Table 1) and in this dilute, far from physiological, environment the deposition of matrix is very tardy.

TABLE 1

Concentration of solids in conventional cell culture system

| MEDIA | COMPANY | SOLID CONCENTRATION |
|---|---|---|
| Minimum Essential Medium | Invitrogen, Cat. No: 10370021, 10370039, 10370047, 10370054, 10370070 | 11.52 g/l |
| F12 Nutrient Mixture | Invitrogen, Cat. No: 21765029 | 11.87 g/l |
| RPMI 1640 Medium | Invitrogen, Cat. No. 11835030, 11835055, 11835063, 11835071 | 12.39 g/l |
| Ham F10 Nutrient Mixture | Invitrogen, Cat. No. 22390017, 22390025 | 16.55 g/l |
| DMEM: F12 Medium | ATCC, Cat. No. 30-2006 | 16.78 g/l |
| DMEM High Glucose (4.5 g/) and L-glutamine | Invitrogen, Cat. No. 41965039, 41965047 | 17.22 g/l |

In an attempt to modulate the in vitro micro-environment and closely emulate the in vivo setup, macromolecules have been used to crowd the culture media (Table 2). Under crowded conditions, thermodynamic activities increase by several orders of magnitude and biological processes, such as enzymatic activities and protein folding can be dramatically accelerated.

TABLE 2

Macromolecules that have been used to-date as crowding agents

| CROWDER USED | RESULTS | REFERENCE |
|---|---|---|
| Sucrose and glucose (monomers for dextran and Ficoll ™), PEG 0.2 Kda Ficoll ™ 70 Kda, Dextran T70 Kda, PEG 8 Kda, PEG 35 KDa | Ineffective MMC significantly increased enzymatic activity | Zimmermann and Harrison, 1987, PNAS, 84: 1871-1875 |
| Ficoll ™ 70 KDa, Dextran 70 KDa | Faster protein folding rates | van den Berg et al., 1999, EMBO Journal, 18(24): 6927-6933 |
| PEG 3.5 Kda, Ficoll ™ 70 KDa | MMC dramatically increase fibrillation of unfolded proteins | Munishkina et al., 2008 Biochemistry, 47(34): 8993-9006 |
| Ficoll ™ 70 Kda, Dextran 70 KDa | MMC dramatically accelerated the nucleation step of fibril formation of human Tau fragment & prion protein | Zhou et al., 2009, Journal of Biological Chemistry, 284(44): 30148-30158 |
| Dextran Sulphate 500 Kda (negative; 46 nm radius) PSS 200 Kda (negative; 22 nm radius) Ficoll ™ 400 Kda (neutral; 4.5 nm radius) Ficoll ™ 70 Kda (neutral; 3 nm radius) | Dramatically accelerated extracellular matrix composition | Lareu et al., 2007 FEBS letters, 581: 2709-2714 Lareu et al., 2007 BBRC, 363: 171-177 Lareu et al., 2007 Tissue Engineering., 13(2): 385-391 |

Animal extracted and recombinant collagen is used in several tissue engineering applications since under appropriate conditions of temperature; pH; and ionic strength since they will self-assemble to produce collagen fibres indistinguishable from fibres found in vivo. However, animal extracted collagens are responsible for immune response, whilst recombinant collagen is not biologically active since it is not produced with the appropriate post-translation modifications.

Lareu et at (2007) describe a dramatic enhancement in collagen matrix deposition by using large negatively charged polameric macromolecules to create an excluded volume effect in long fibroblast cultures. Chen et at (2004) similar results were achieved using a cocktail of macromolecules using dextran sulphate and FICOLL™ (neutral branched hydrophilic polysaccharides) molecules. Again the crowders are negatively charged molecules with large hydrodynamic radii. Similarities have been shown with neutral and negatively charged dextran sulphate by Lareu (2007) and Peng and Raghunath.

[In Press]

The present inventors have surprisingly found that by using poly-dispersed macromolecular crowders, that cell metabolism and extracellular matrix production can be enhanced to such a level that significant quantities of tissue substitute films are produced after as little as 48 hours. It has never previously been shown that poly-dispersity of a macromolecule is key to enhancing the production of tissue substitutes. This knowledge allows the identification of molecules which are suitable for this purpose and the mixing of molecules to enhance the polydispersity of a mixture of molecules.

Object of the Invention

It is thus an object of the present invention to provide a process for the production of tissue substitutes or artificial tissue constructs which is rapid. These tissue substitutes or constructs can take the form of tissue layers or sheets of cells. In particular the object of the invention is to provide a method of producing commercially viable quantities of tissue substitute films within a period of 2-5 days. In particular it is an object of the invention that the substitute can be produced within in about 48 hours.

Another object is to address the shortfalls of animal-extracted and recombinant molecules and to provide a new method for producing tissue substitutes without the addition of any animal compounds. Such a product would harbour no risks for interspecies transmission of disease (as compared to animal extracted collagen) and also is fully biologically active (as opposed to recombinant collagen) since it is produced naturally from cells.

The presence of macromolecules in the culture media will closely emulate the in vivo setup and facilitate the fast deposition of extracellular matrix as typified by collagen type I (FIG. 3) or fibronectin production. It is an object to apply the principles of macromolecular crowding on human fibroblast cultures are applied to produce, isolate and purify for first time a human tissue substitute that can be used as raw material for biomedical devices or in tissue repair or regeneration. This tissue produced will have advantages over recombinant technologies since it will be fully biologically functioning (produced from human cells) and will avoid the risk of interspecies transmission of disease, since no animal serum is used. Moreover, this system can facilitate rapid production of host-specific tissue substitutes from the patient's own cells and as such will avoid even immune rejection problems from implantation of materials from another subject.

The presence of macromolecules in the culture media will closely emulate the in vivo setup and facilitate the fast deposition of collagen type I (FIG. 4). Moreover, it is an object that other extracellular matrix molecules will be deposited (e.g. fibronectin). In vitro studies have demonstrated that fibronectin deposition is necessary for the formation of collagen fibrils to occur in the ECM.

An object is to employ the principles of macromolecular crowding on human cells and produce live human cell sheets for tissue engineering and regenerative medicine applications. This system will facilitate production of host-specific cell-based scaffolds from the patient's own cells and as such will avoid immune rejection problems from implantation of materials from another subject. In addition, this system can also be used to produce host specific proteins (e.g. collagen) that can be used for tissue engineering applications. Moreover, this system can be used to accelerate in vitro biological processes (e.g. enzyme activity; degradation of proteins, etc).

The tissues so produced may be used for tissue engineering applications. Such applications include Tendon regeneration, Bone regeneration, Nerve regeneration, Cornea regeneration, Skin regeneration etc, Drug delivery, drug discovery, gene discovery, In vitro systems (e.g. development of cancer therapeutics; development blood-brain barried systems, etc) Gene delivery, coating of medical devices to avoid immune response, and tissue glues/adhesives.

Such products will replace products that are based on animal extracted molecules and products that are based on human recombinant molecules.

SUMMARY OF THE INVENTION

According to the present invention there is provided a method for the production of a tissue substitute comprising culturing cells in the presence of one or more macromolecular crowders, wherein the macromolecular crowders are large poly-dispersed macromolecules. Two or more macromulecular crowders may be preferred. The macromolecules may be negatively charged or neutral macromolecules.

The large poly-dispersed macromolecules may be selected from the group comprising carrageenan, dextrans, dextran sulphate, FICOLL™ (neutral branched hydrophilic polysaccharides), bovine serum albumin, sodium alginate, polyethylene glycol, sepharose-CL and polysodium-1-styrene sulphonate. Particularly preferred is carrageenan. Carageenan may be used in combination with one or more of the molecules as defined above.

The invention may comprise a method of producing a tissue substitute comprising culturing cells in the presence of a large macromolecular crowder with the proviso that the crowder is not dextran sulphate alone. In other words, dextran sulphate is used with another crowder.

Carrageenans are a family of linear sulphated polysaccharides extracted from red seaweeds. There are several types of carrageenan:—Kappa, lambda and iota, all of which would be suitable for use in this invention. Particularly preferred is kappa carageenan. Also preferred is lambda carrageenan. The macromolecular crowder may be used at between 75 µg/ml and 37.5 mg/ml, with the amount used depending on the size of the crowder.

The cells may be selected from lung fibroblasts, skin fibroblasts, corneal fibroblasts, dermal fibroblasts, human umbilical artery smooth muscle cells, human tenocytes and normal human osteoblasts.

The cells may be cultured in the presence of culture medium supplemented with fetal bovine serum, human serum, ascorbic acid phosphate, or a combination thereof. The human serum may be used at 0.1% to 40% volume to volume. Suitable concentrations of serum include, 0.5% to 30%, and 5% to 20%.

The invention also provides a cell matrix film, tissue sheet or tissue substitute whenever produced by a method as described above.

As used herein the term "molecules" includes molecules, spheres, particles and polymers. Table 2 indicates the radius for a number of molecules, but should not be taken to imply that all of the molecules of the invention are spheres. As used in here the term "poly-dispersed" means that the molecules have a broad range of size, shape and mass characteristics, as opposed to molecules which have a uniform size, shape and mass distribution which are mono-dispersed molecules. Polymer materials are poly-dispersed if their chain length varies over a wide range of molecular masses. This poly-dispersity can be seen in FIG. 11A-E. A number of neutral and negatively charged macromolecules are poly-dispersed. It is however apparent from the figure that carrageenan is the most poly-dispersed of the molecules tested in this invention, and the inventors hypothesis that this is the reason for the superiority of carrageenan amongst the molecules tested in the method of the present invention. It would however be possible to increase the polydispersity of the crowder, by using a combination of two or more crowders. For example, a mixture of carrageenan and dextran sulphate would be more poly-dispersed than carrageenan alone.

This invention enables the production of substantial amounts of cell tissue within only 48 h, whilst the current in vitro systems take in excess of 6 weeks to produce the same amount of tissue.

To further eliminate animal products from the process, human serum was used and it surprisingly increased further the tissue and extracellular matrix production as typified by collagen production. A number of cell types were screened (e.g. lung fibroblasts, skin fibroblasts, smooth muscle cells) and surprisingly, it was found that smooth muscle cells can be very rapidly produced by the method of the invention. It was also found that poly-dispersed macromolecules occupy more space and facilitate higher collagen production in comparison to mono-dispersed molecules, indicating higher tissue layer production. Low serum concentration is sufficient for high collagen production which makes this invention even more financially viable. Ultimately, herein we describe for very first time the rapid production of human tissue substitutes that can be used for any tissue engineering applications.

BRIEF DESCRIPTION OF THE DRAWINGS

FIG. 11A-E: Poly-dispensity levels of macromolecules: The size dispersion by intensity confirms that the negatively charged macromolecules (carrageenan, dextran sulphate and PSS) are highly polydispersed and among them, carrageenan is the most polydispersed.

FIG. 15A-F: The morphology for WI38 and WS1 and smooth muscle cells was not affected independent of the serum concentration, the macromolecule; and the period in culture.

DETAILED DESCRIPTION OF THE DRAWINGS

Figure 1:
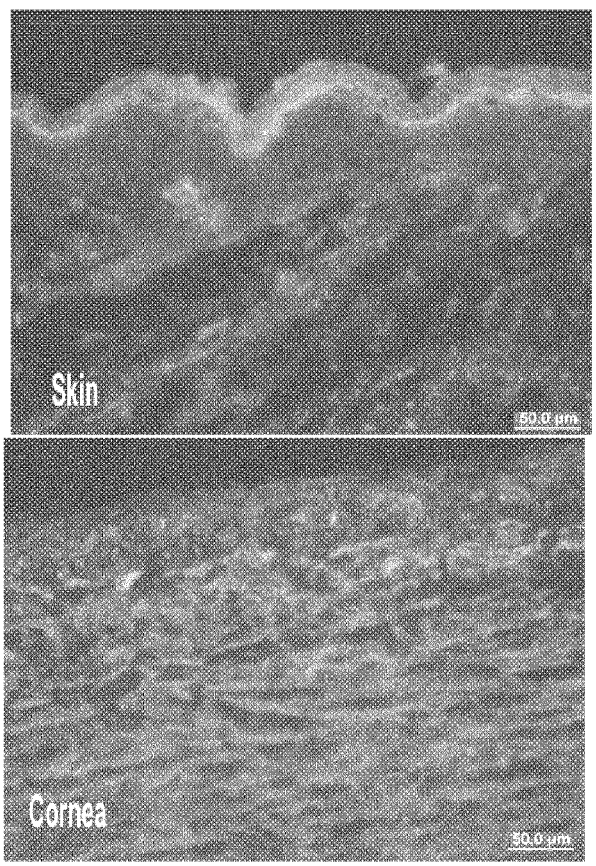
FIG. 1: Immunofluorescent images of skin and cornea tissue. Cells (stained blue with DAPI) are packed in the dense extracellular matrix.
Figure 2:
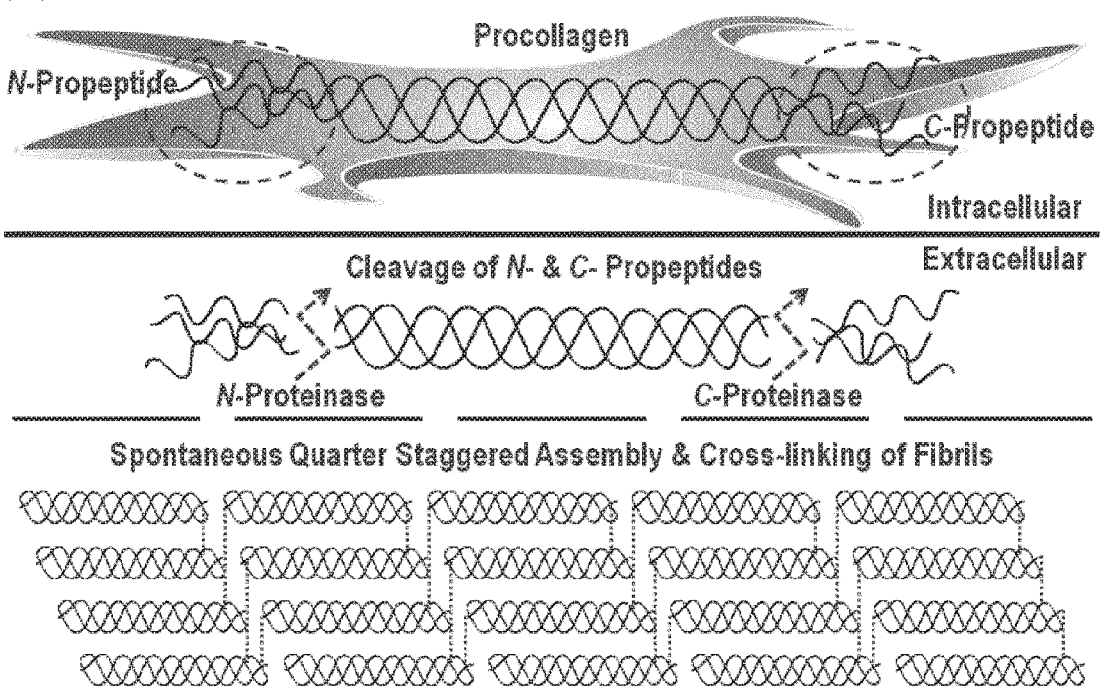
FIG. 2: In vivo collagen biosynthesis. Cells synthesise collagen with intact pro-peptide extensions. During, or following, secretion in the heavily crowded extracellular space, pro-peptide cleavage by specific proteinases takes place that triggers the spontaneous quarter staggered self-assembly of collagen molecules into fibrils. Subsequently, the native cross-linking pathway of lysyl-oxidase takes place that give rise to collagen fibres.
Figure 3:
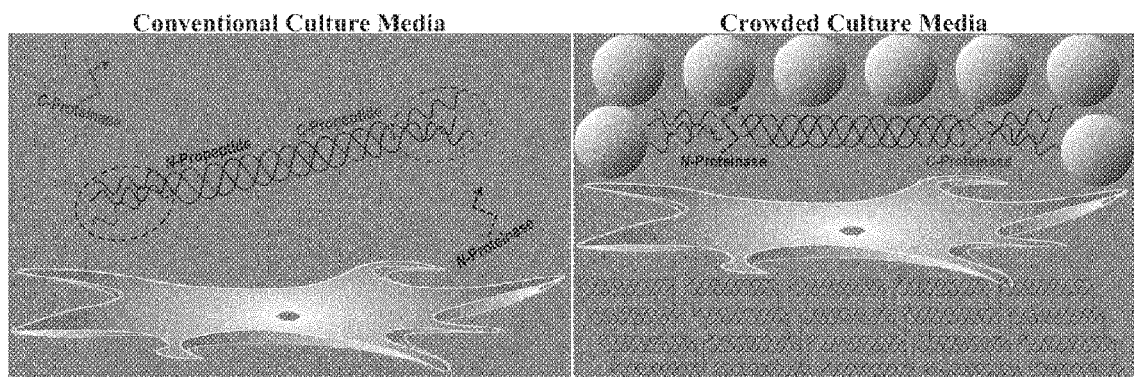
FIG. 3: In conventional cell-culture system the collagen deposition is very slow due to the very dilute, far from physiological, conditions (left panel). However, under crowding conditions, the pro-peptide extensions are cleaved by the specific proteinases and collagen deposition takes place (right panel).
Figure 4:
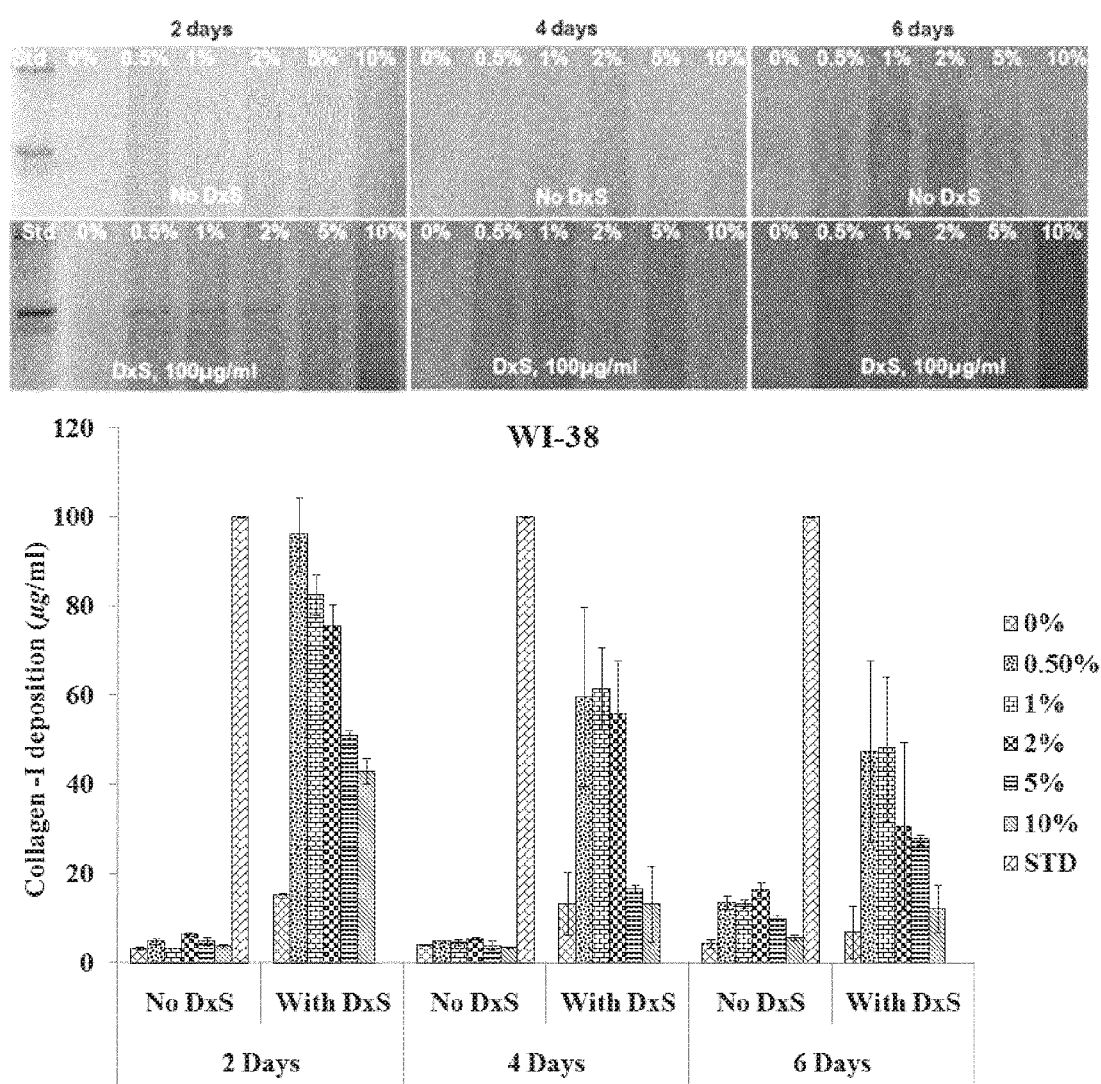
FIG. 4: SDS-PAGE and complimentary densitometric analysis demonstrated that WI-38 fibroblasts at the presence of 500 Kd DxS (100 µg/ml) deposited highest amount of ECM after 2 days in culture and at FBS concentration between 0.5 and 1%. Standard: 100 µg/ml bovine collagen type I (Symatese Biomateriaux, France).
Figure 5:
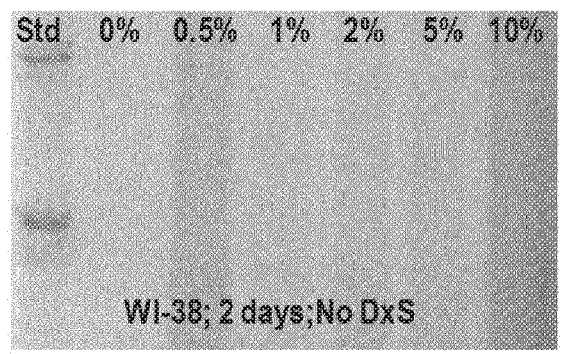
FIG. 5: (top) SDS-PAGE and complimentary densitometric analysis indicates that the 0.5% and 1% serum concentration facilitates maximum ECM deposition for WI38 and WS1 fibroblasts (p<0.001) after 2 days in culture at the presence of 100 µg/ml 500 KDa dextran sulphate. SDS-PAGE analysis indicates the 0.5% serum concentration facilitates maximum collagen type I deposition for WI38 fibroblasts. For the WS1 fibroblasts no difference was observed in collagen deposition for 0.5% and 1% serum concentration and both these concentration facilitated higher collagen deposition than any other serum concentration after 2 days in culture at the presence of dextran sulphate (bottom) Complementary densitometric analysis confirms the high deposition of collagen type I under crowded conditions at 0.5% serum concentration for both WI38 and WS1 fibroblasts.
Figure 5:
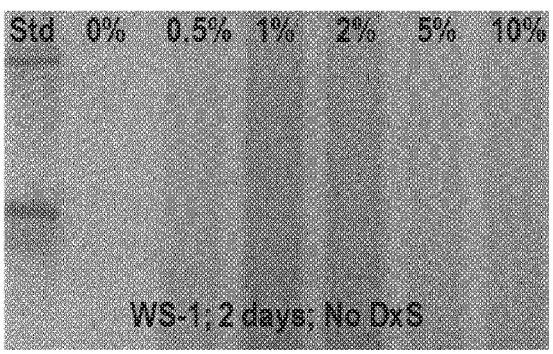
Figure 5:
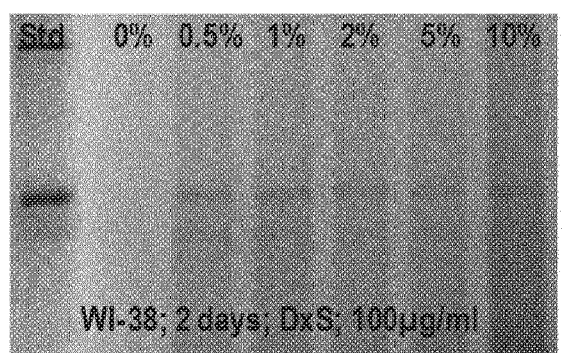
Figure 5:
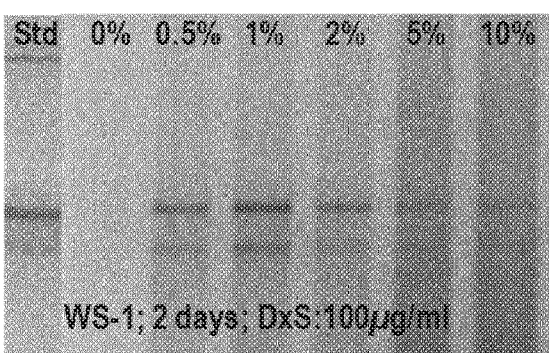
Figure 5:
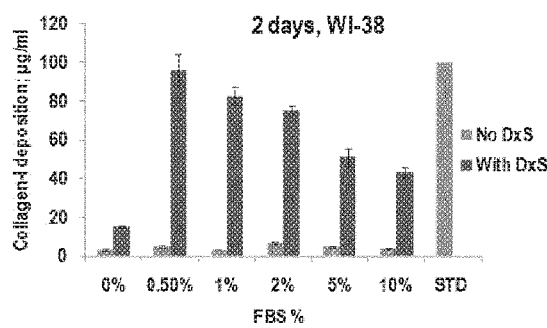
Figure 5:
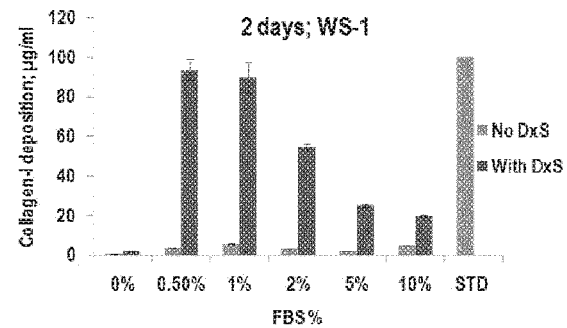
Figure 6:
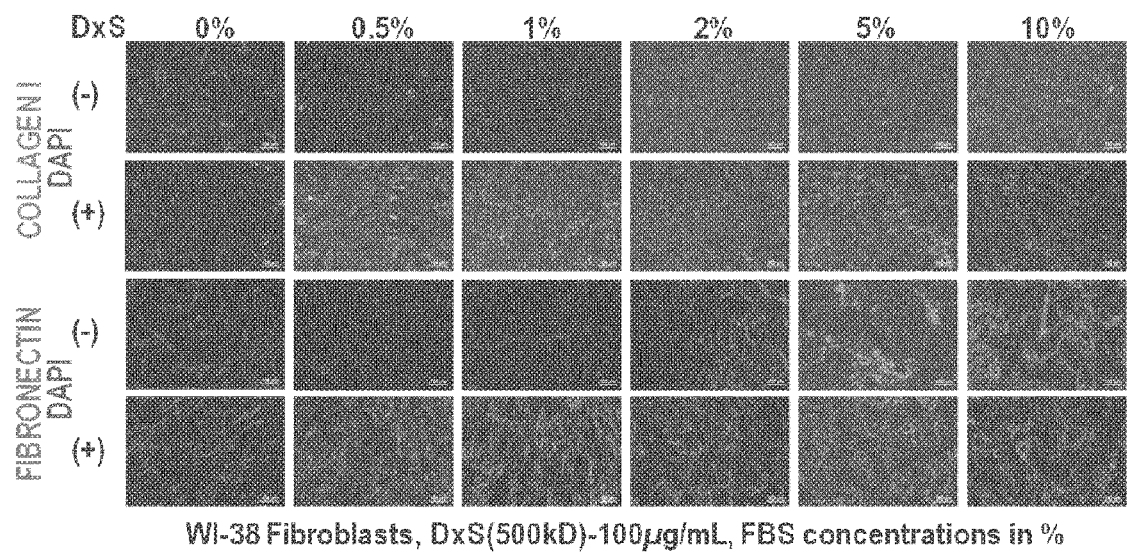
FIG. 6: Immunocytochemistry experimentation demonstrates the high deposition of collagen type I and fibronectin after 2 days in WI38 culture, at 0.5% and 1% serum, at the presence of dextran sulphate. Co-localisation of fibronectin and collagen type I is also apparent.
Figure 7:
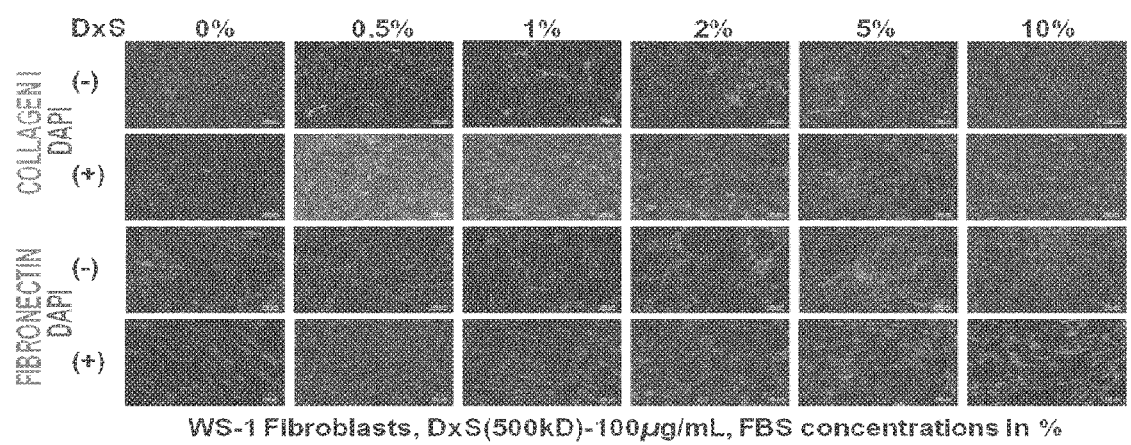
FIG. 7: Immunocytochemistry experimentation demonstrates the high deposition of collagen type I and fibronectin after 2 days in WS1 culture, at 0.5% serum, at the presence of dextran sulphate. Co-localisation of fibronectin and collagen type I is also apparent.
Figure 8:
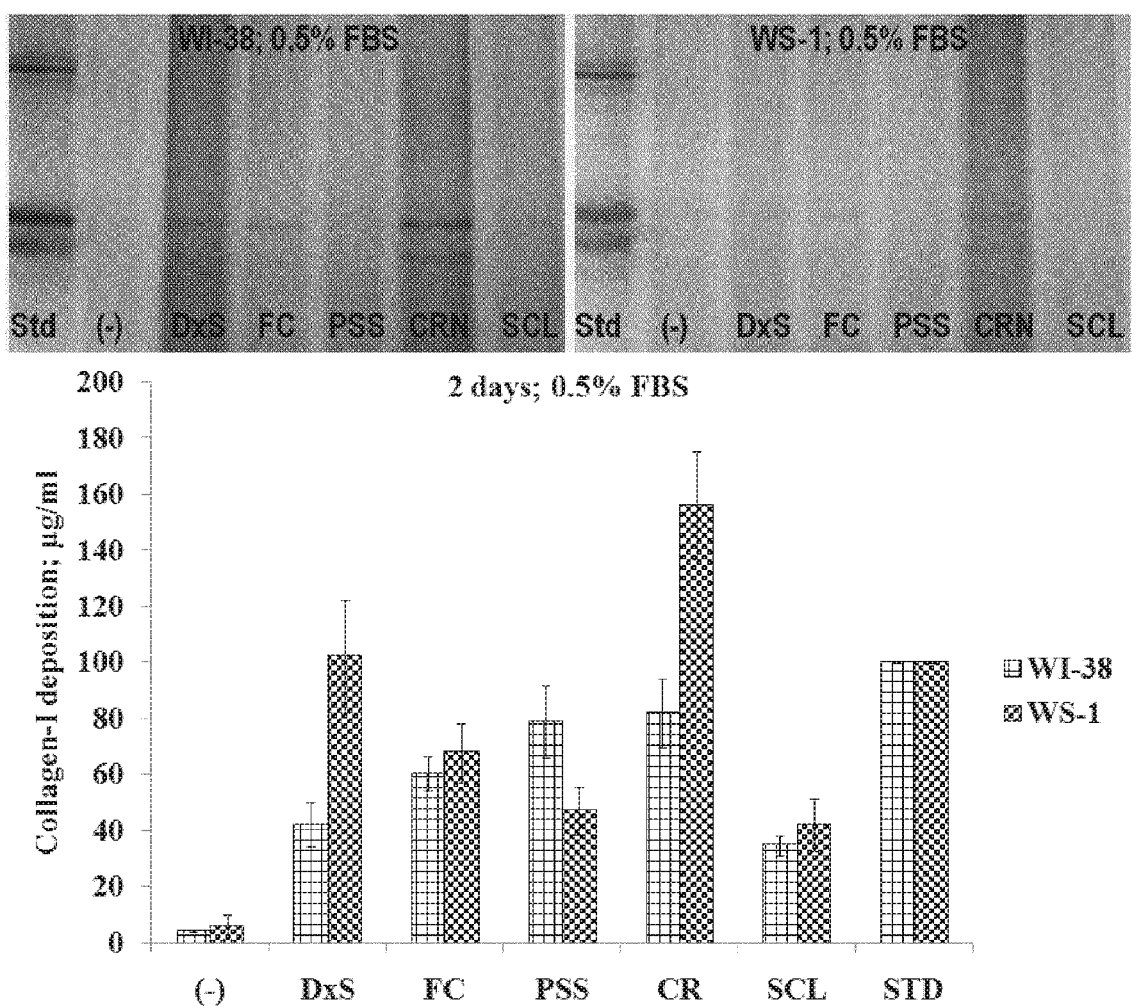
FIG. 8: SDS-PAGE analysis indicates the highest collagen deposition in WI38 and WS1 culture in the presence of carrageenan.
Figure 9:
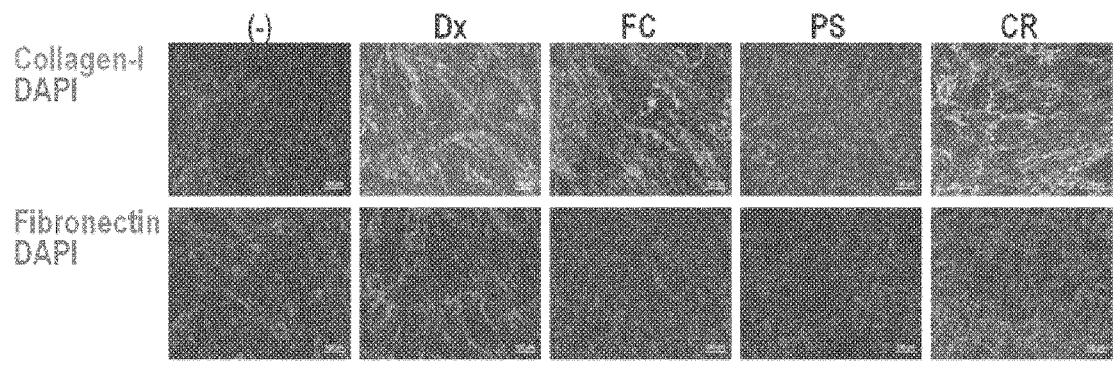
FIG. 9: Immunocytochemistry experimentation corroborated the high collagen type I deposition at the presence of carrageenan in the culture of WI38 and WS1 fibroblasts after 2 days in culture.
Figure 9:
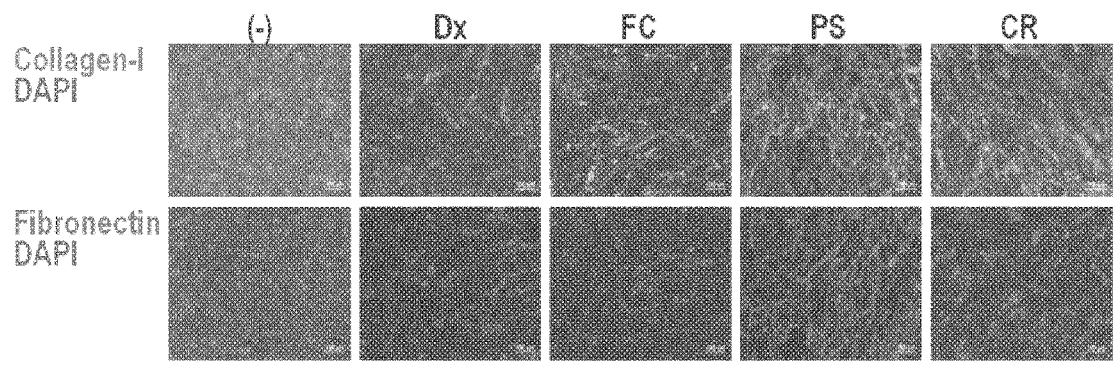
Figure 10:
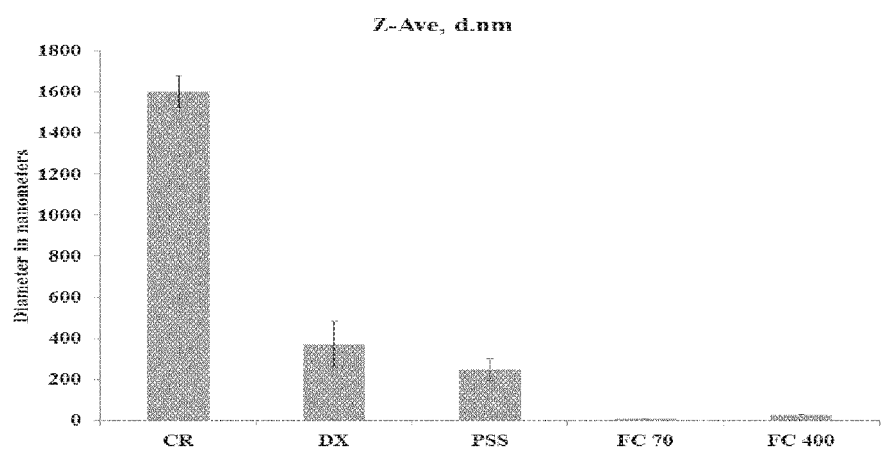
FIG. 10: The dynamic light scattering analysis demonstrated that the negatively charged macromolecules (carrageenan, dextran sulphate and PSS) had significant higher hydrodynamic diameter (Z-Ave, d.nm) than their neutral counterparts FICOLL™ 70, FICOLL™ 400 (neutral branched hydrophilic polysaccharides)).
Figure 11C:
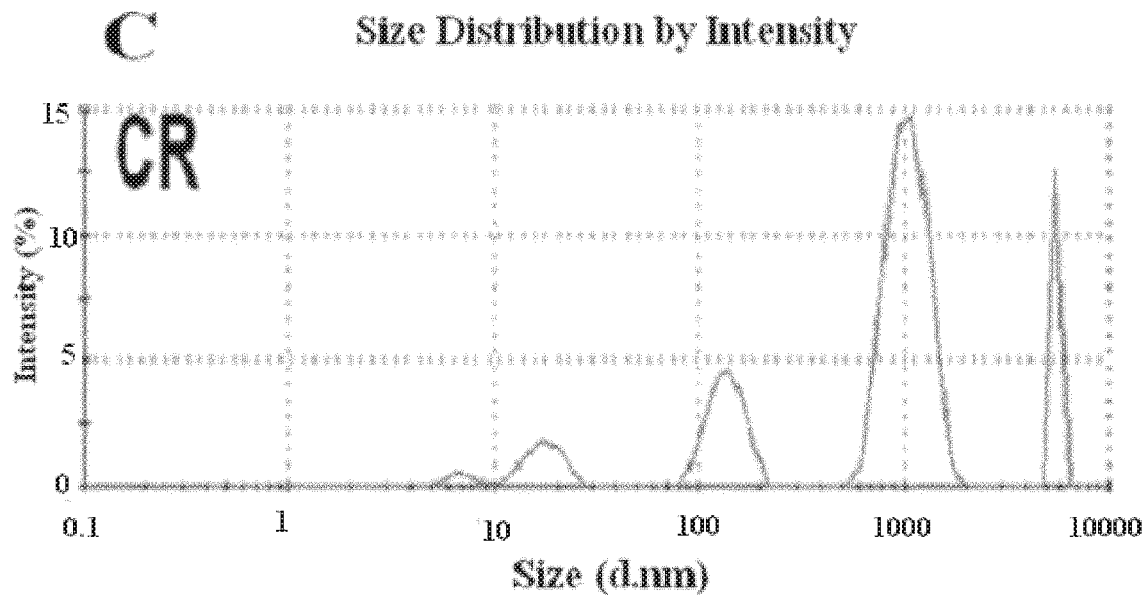
Figure 11D:
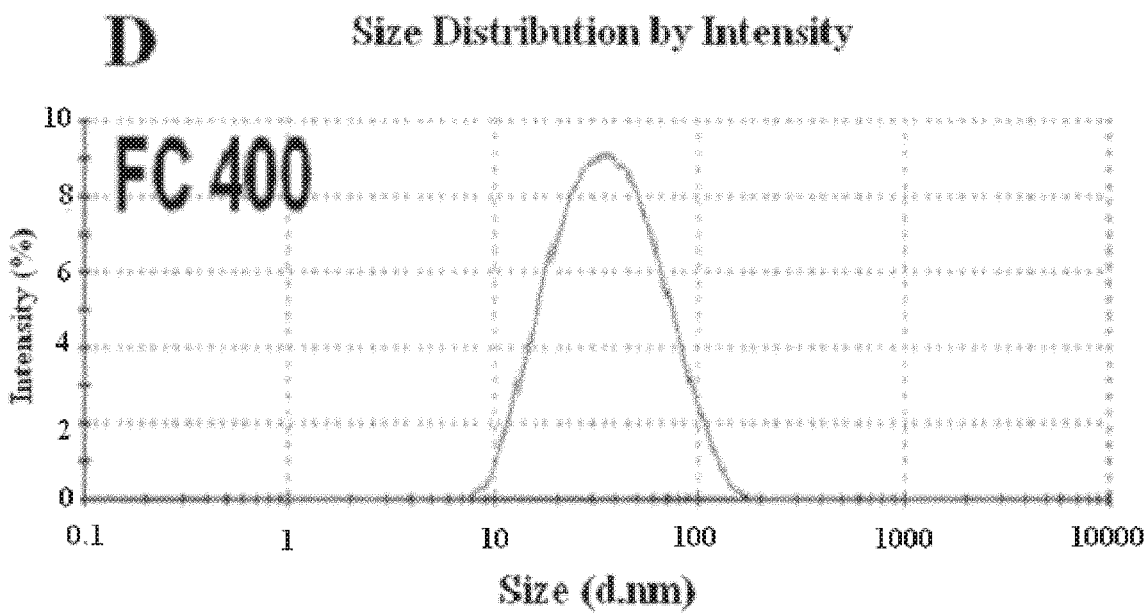
Figure 11E:
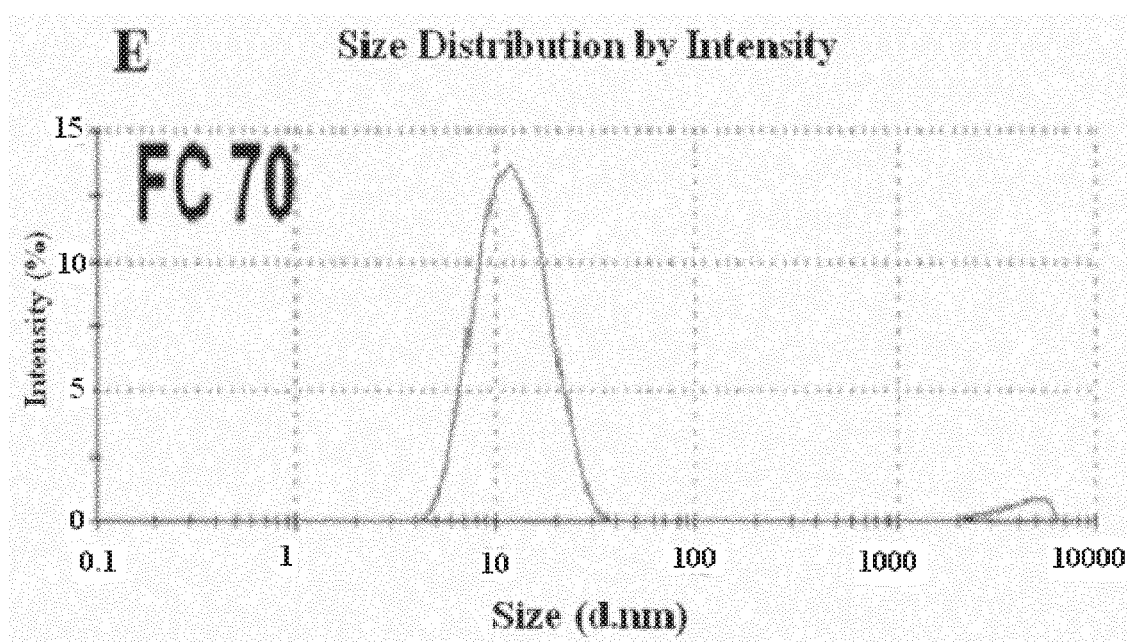
Figure 12:
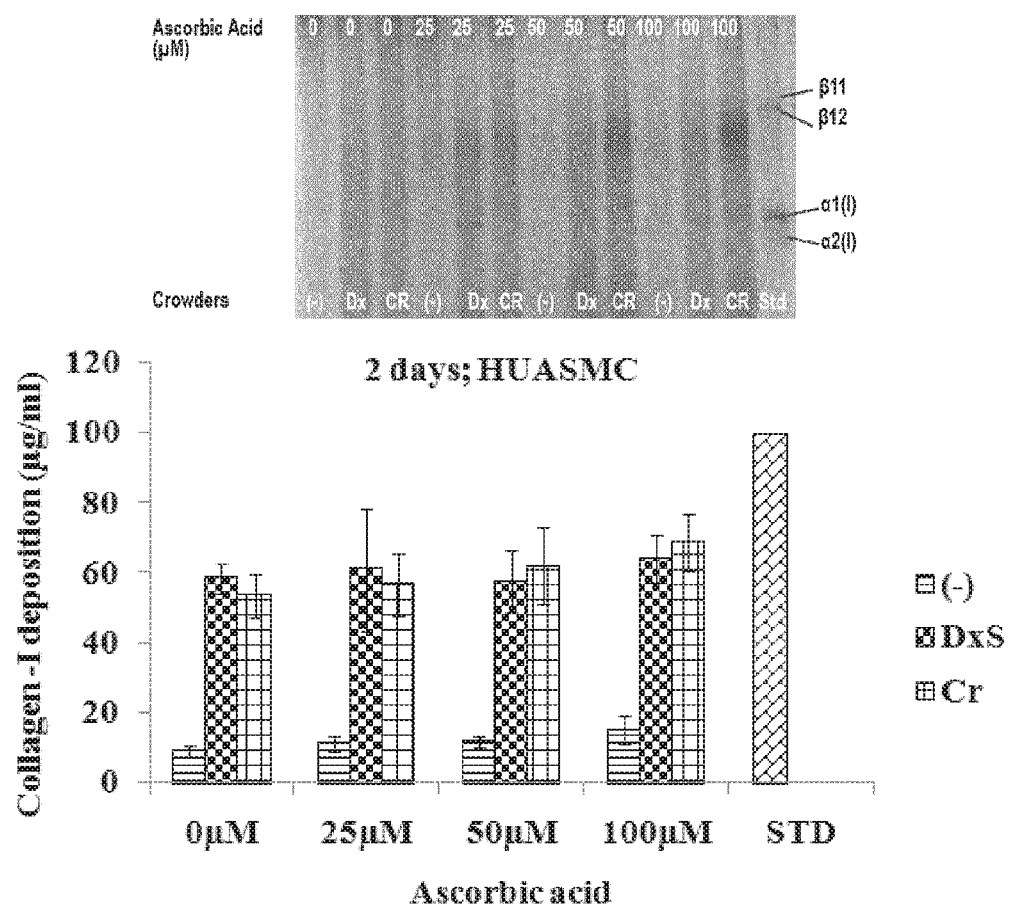
FIG. 12: The influence of macromolecular crowding in human umbilical smooth muscle cells in the presence of various concentrations of ascorbic acid.
Figure 13:
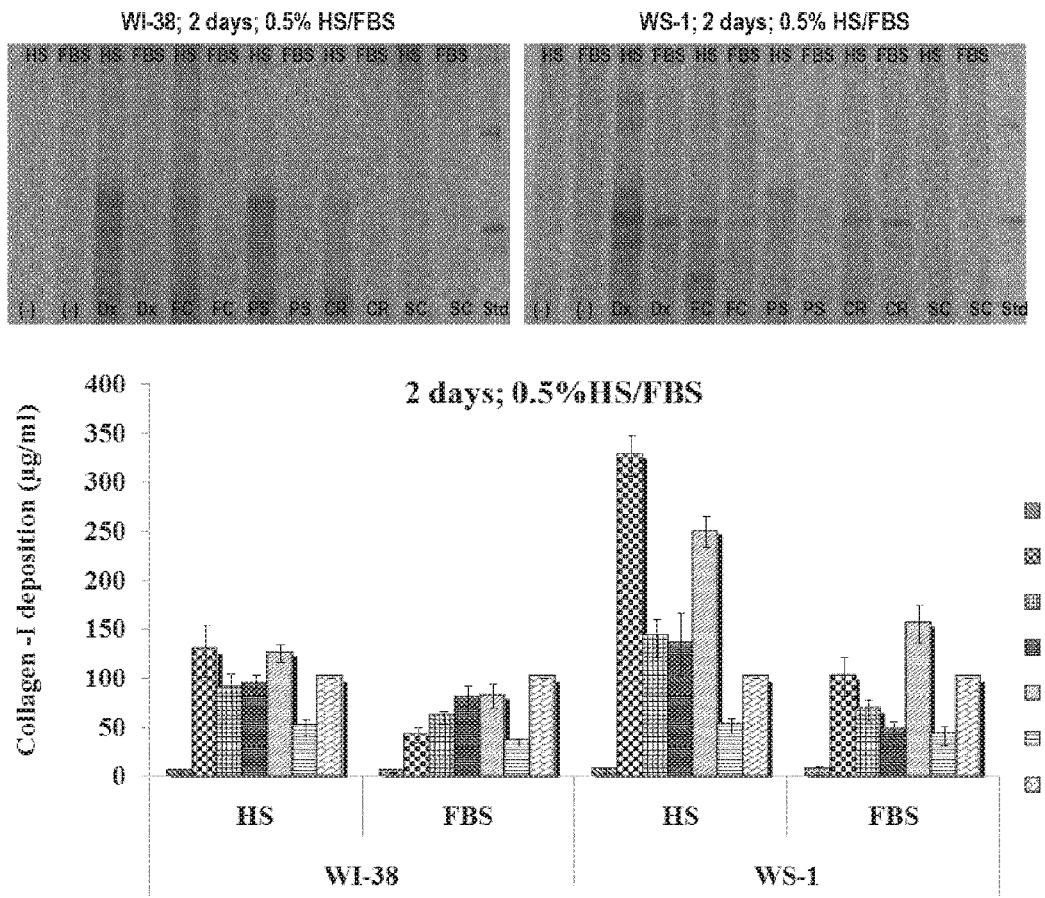
FIG. 13: SDS-PAGE and complementary densitometric analysis indicates that human serum induced higher ECM deposition in comparison to FBS counterparts.
Figure 14:
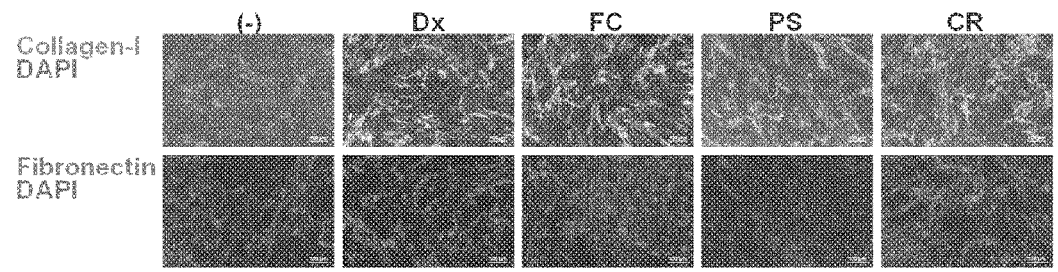
FIG. 14: Immunocytochemistry evaluation further corroborated the higher ECM deposition in the presence of human serum, when compared to FBS in the culture of WS1 and WI38 fibroblasts.
Figure 14:
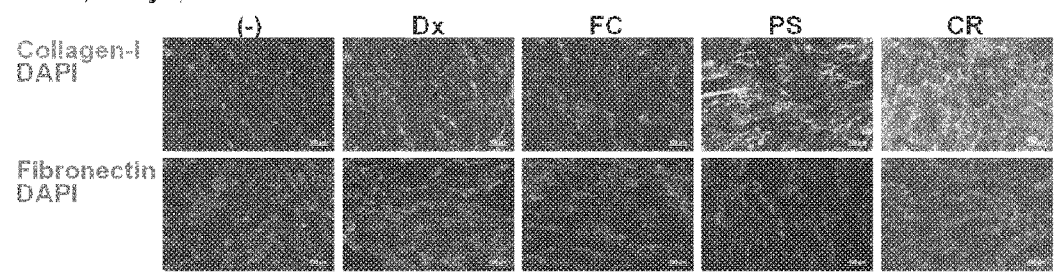
Figure 15A:
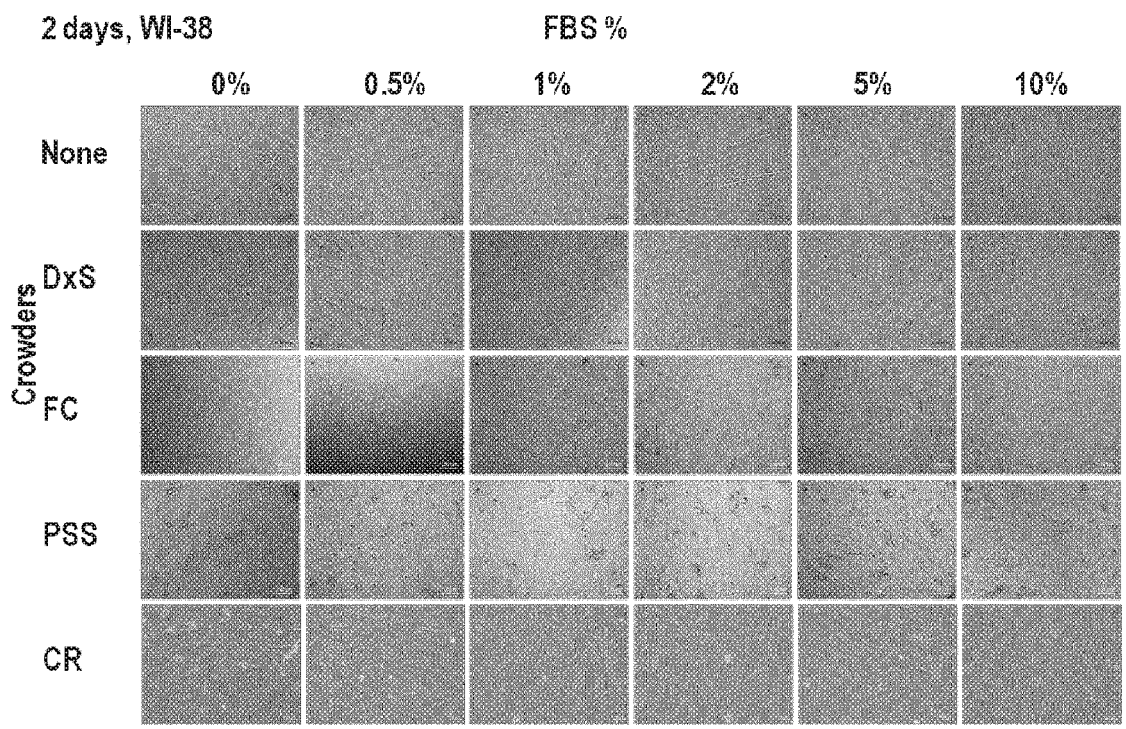
Figure 15B:
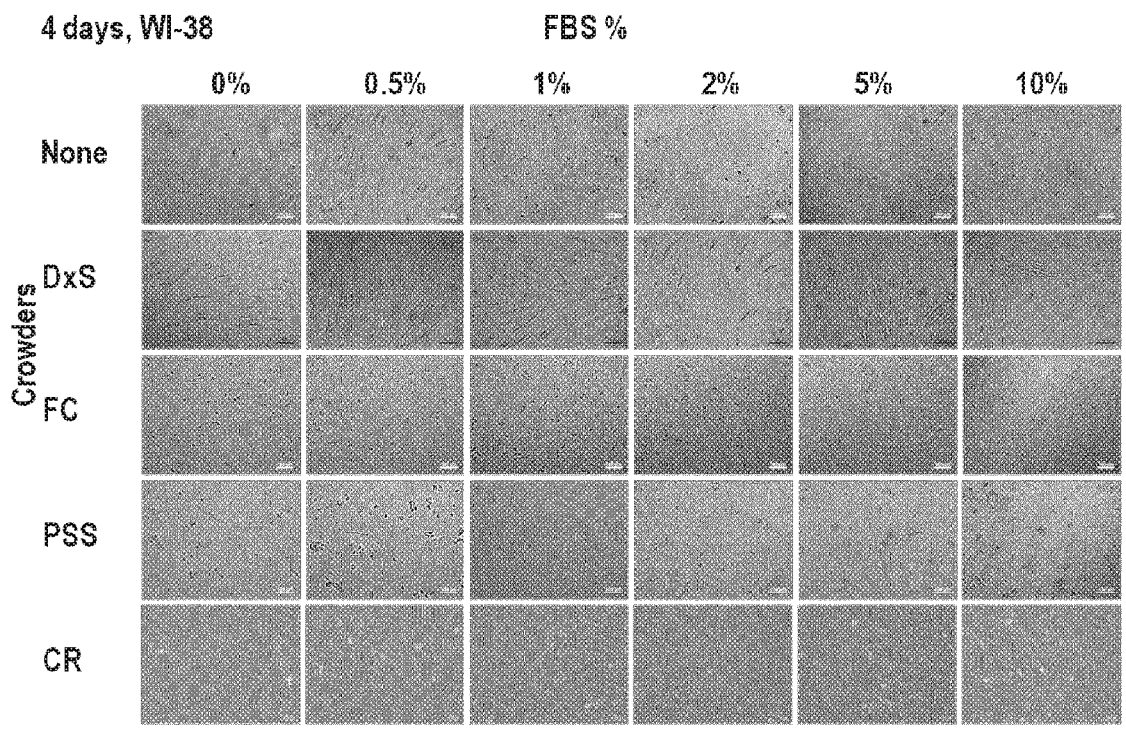
Figure 15E:
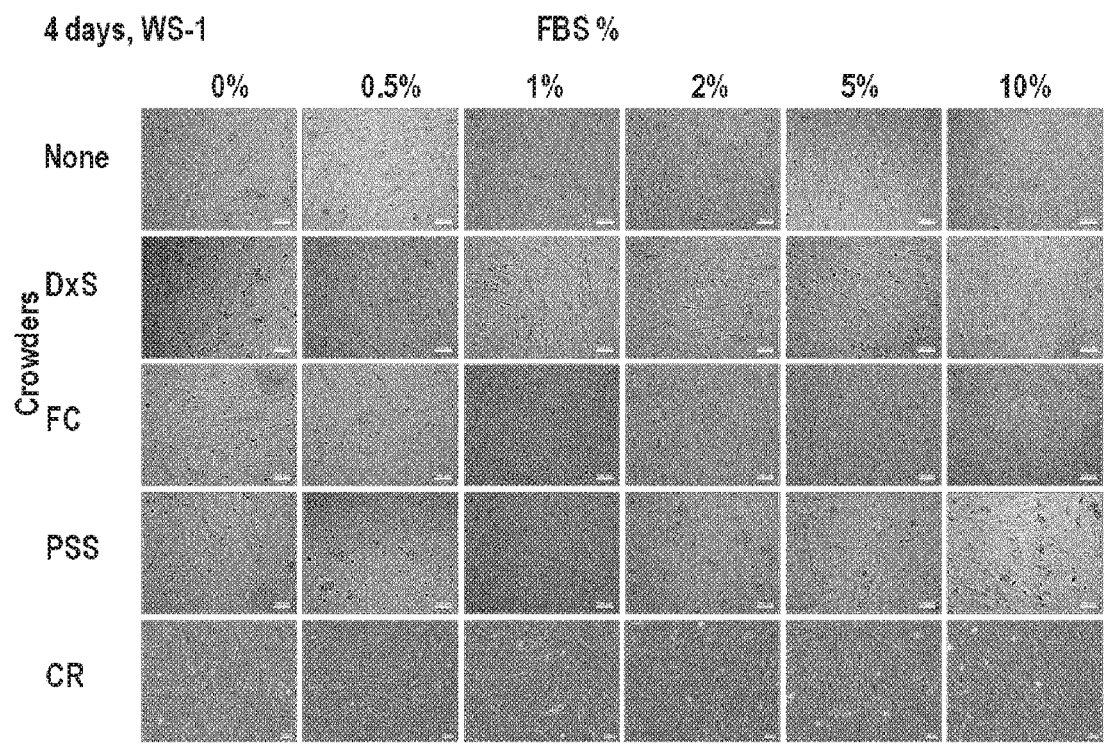
Figure 15F:
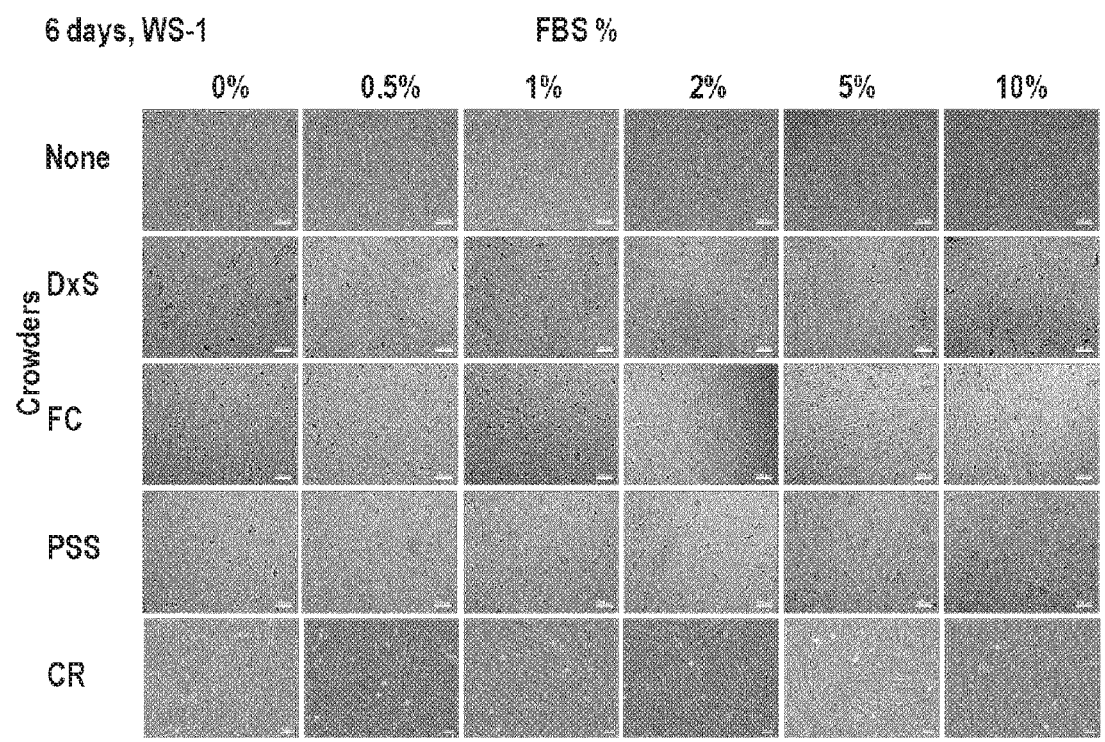
Figure 16:
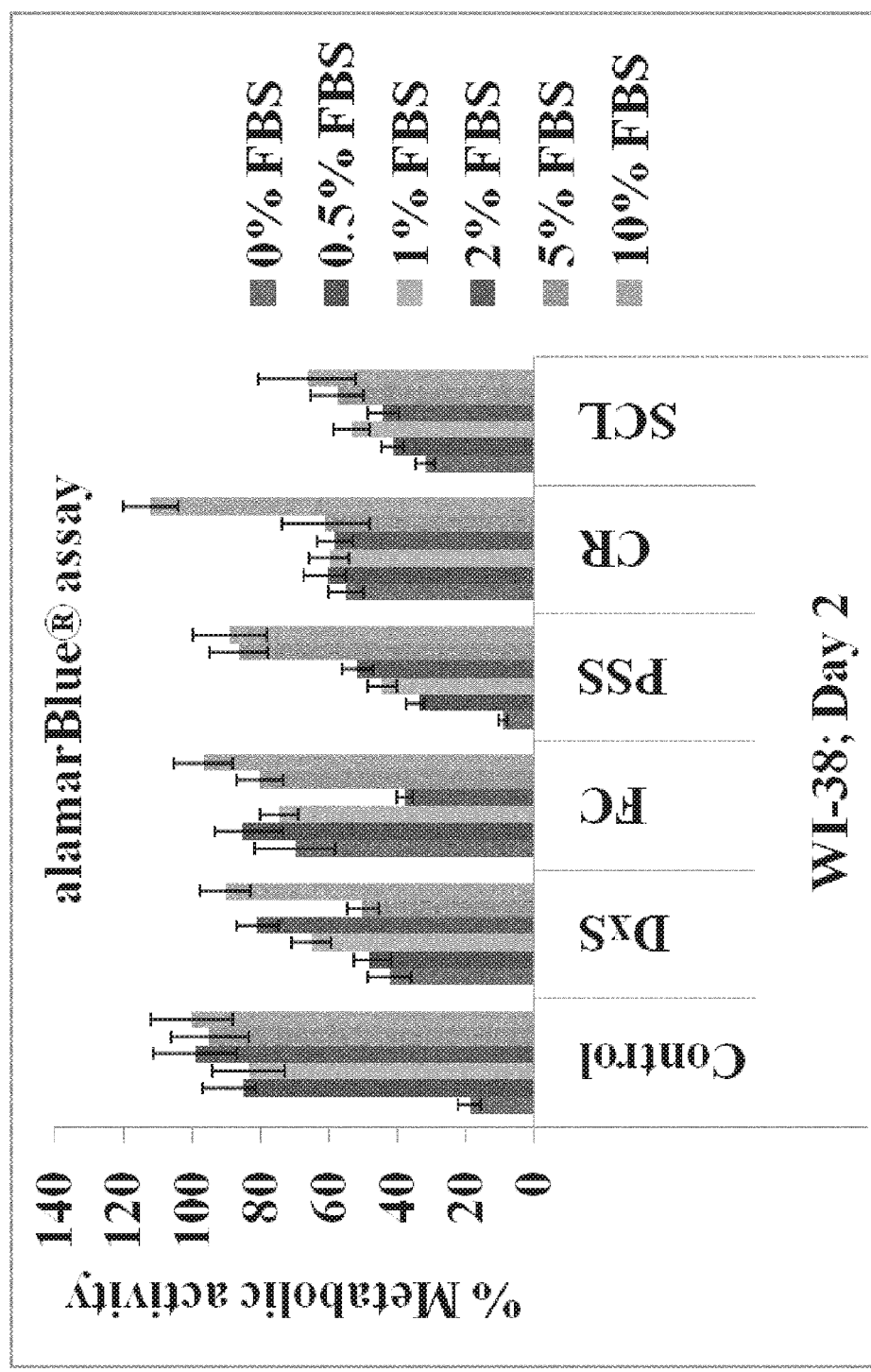
FIG. 16: A Lamar BLUE™ results as a function of FBS concentration statistics.
Figure 17:
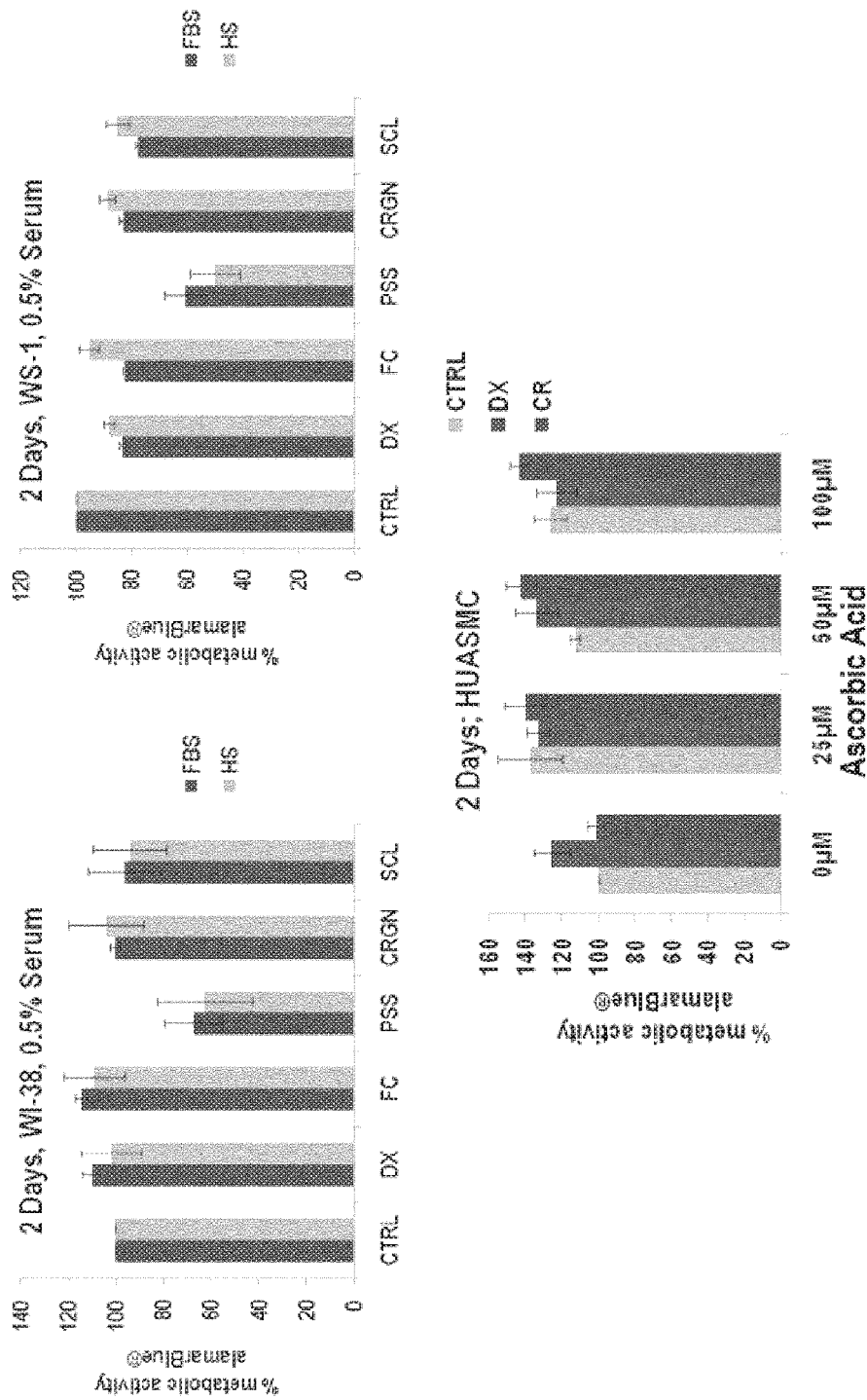
FIG. 17: A Lamar BLUE™ results as a function of FBS concentration statistics.
Figure 18:
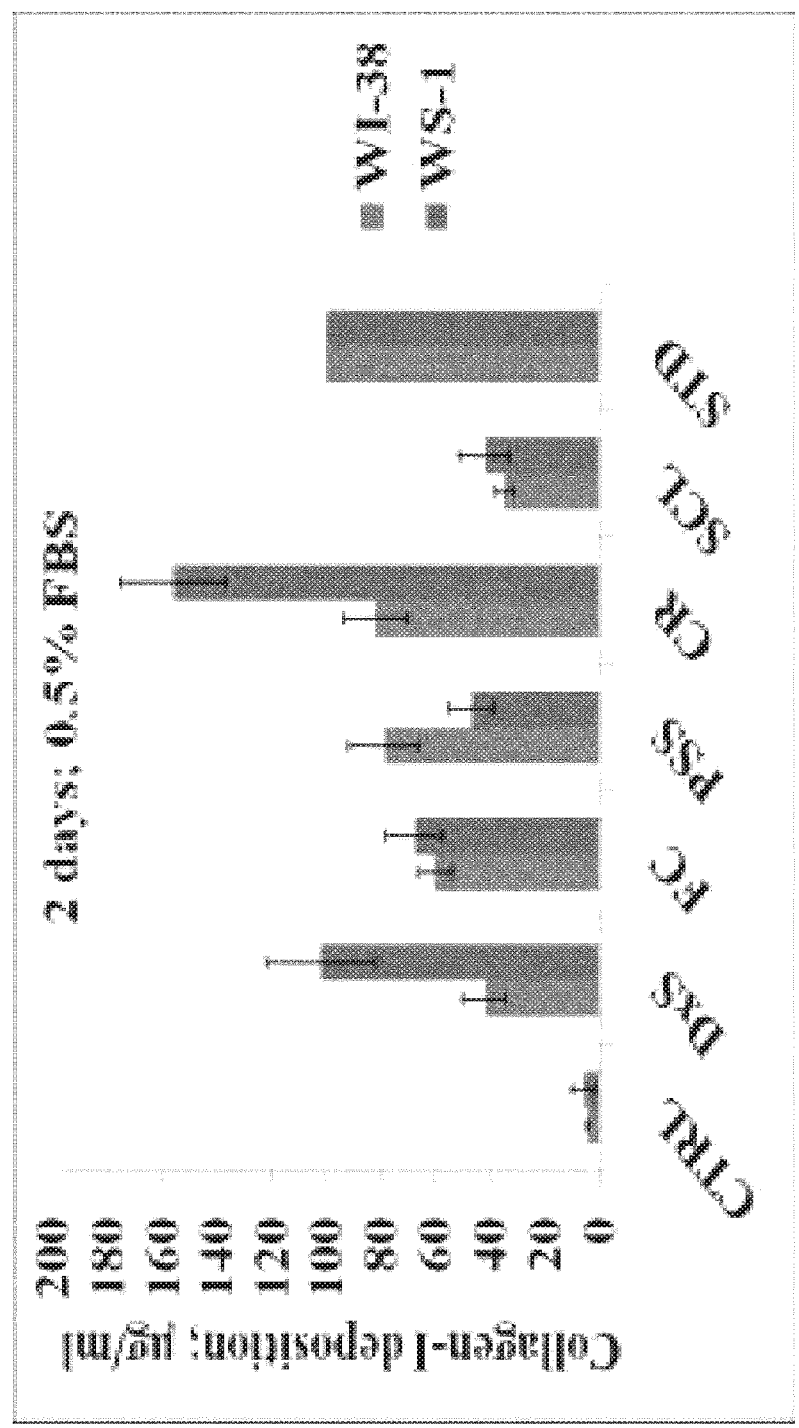
FIG. 18: Complementary densitometric analysis shows that carrageenan induces maximum collagen deposition in WS1 and WI38 fibroblast culture.
Figure 19:
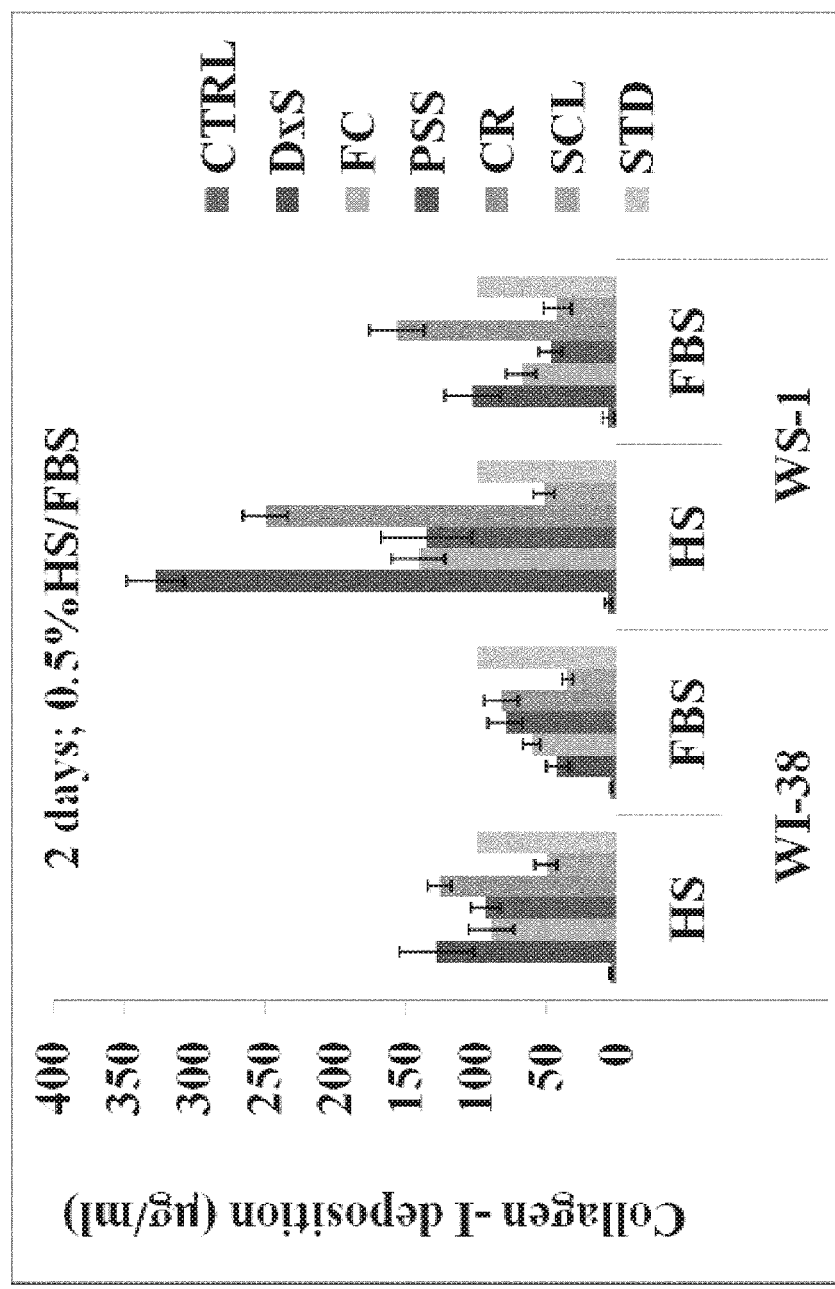
FIG. 19: Complementary densitometric analysis shows that human serum increased collagen deposition in WS1 and WI38 fibroblast culture when compared to FBS.

Materials and Methods
Cell Culture:
Human lung fibroblasts (WI-38; American Tissue Culture Collection), Human skin fibroblasts (WS-1; American Tissue Culture Collection) were routinely cultured in Dulbecco's modified Eagle medium with 10% fetal bovine serum (FBS), 1% penicillin-streptomycin at 37° C. in a humidified atmosphere of 5% $CO_2$. Commercially available Smooth Muscle Growth Medium-2 (CLONETICS® SmGM®-2) and supplements (SmGM-2 SingleQuots) were used for human umbilical arterial smooth muscle cells (HUASMC; CLONETICS® UASMC-Human Umbilical Artery Smooth Muscle Cells; Lonza CC-2579). Cells were seeded at 50,000 cells/well in 24-well plates and were allowed to attach for 24 hours. After 24 hours the medium was changed with medium containing macromolecular crowders (100 µg/ml dextran sulphate 500 kDa; 37.5 mg/ml FICOLL™ 70 and 25 mg/ml FICOLL™ 400 (neutral branched hydrophilic polysaccharides); 100 µg/ml Polysodium-4-Styrenesulfonate, 75 µg/ml carrageenan and 100 µl/ml sepharose-CL) and with various percentages of FBS (0%, 0.5%, 1%, 2%, 5%, and 10%). To induce collagen synthesis, fibroblasts were supplemented with 100 µM L-ascorbic acid phosphate. The HUASMC was supplemented with various concentration of ascorbic acid (0 µM, 25 µM, 50 µM and 100 µM). In some of the experiment commercially available human serum (Lonza, Belgium) was also used as supplement in place of FBS.

Phase Contrast Microscopy:
The influence of various crowders and FBS percentages on cell morphology was evaluated using phase-contrast microscopy at day 2, 4 and 6. Images of the cells were taken by inverted microscope (Leica microsystem, Germany) and images were analyzed with the help of LAS EZ 2.0.0 software.

Collagen Extraction:
At the end of culture time points, culture media were collected into separate vials, whereas cell layers were washed twice with Hank's balanced salt solution (HBSS). Both culture medium and washed cell layer were digested with porcine gastric mucosa pepsin in a final concentration of 1 mg/ml in 0.5M acetic acid. Samples were incubated at 37° C. for 2 hours with gentle shaking followed by neutralization with 0.1 N NaOH.

Sodium Dodecyl Sulfate-Polyacrylamide Gel Electrophoresis (SDS-PAGE):

Cell layer and Medium samples were analyzed by SDS-PAGE under nonreducing conditions with Mini-Protean 3 (Bio-Rad Laboratories). 100 µg/ml of bovine collagen type I (Symatese biomateriaux, France) was used as standards with every gel. Protein bands were stained with the SilverQuest® kit (Invitrogen) according to the manufacturer's protocol. Densitometric analysis of gels was performed with the help of GeneTools analysis software (Syngene). Collagen bands were quantified by defining each band with the rectangular tool with background subtraction.

Immunocytochemistry:

Fibroblasts were seeded on 4-well LAB-TEK™ II chamber slides at 50,000 cells/chamber and after 24 hours of seeding cells were treated with crowders. After 2 days of culture, medium was removed and cell layers were washed with HBSS and fixed with 2% paraformaldehyde at room temperature for 15 min. After several washes in phosphate-buffered saline (PBS), nonspecific sites were blocked with 3% bovine serum albumin in PBS for 30 min. The cells were incubated for 90 min at room temperature simultaneously with Collagen I (Rabbit anti-human): dilution 1:100 and Fibronectin (Mouse anti-human) dilution 1:200 for 90 min. Bound antibodies were visualized using Alexa Fluor®488 chicken anti-rabbit and Alexa Fluor®555 goat anti-mouse 1:400 in PBS for 30 min. Post-fixation was with 2% PFA for 15 min. Cell nuclei were counterstained with 4,6-diamidino-2-phenylindole (DAPI) and slides were mounted with VECTASHIELD® mounting media. Images were captured with an Olympus IX-81 inverted fluorescence microscope (Olympus Corporation, Tokyo, Japan).

Dynamic Light Scattering (DLS) Measurements:

Dynamic light scattering (DLS) measurements of macromolecules were done using Zetasizer Nano ZS90 (Malvern Instruments) at 25° C. Molecules were dissolved in HBSS, pH 7.4 for size (Z-Ave; d.nm) measurements, and for zeta (ζ)-potential measurements, macromolecules were dissolved in water. The measurement of zeta (ζ)-potential and size (Z-Ave. diameter in nano meter) were analysed by the help of Zetasizer software 6.12 (Malvern Instruments).

Cell Metabolic Activity (alamarBlue®):

alamarBlue® assay was performed to quantify the influence of various crowders and serum on metabolic activity of the fibroblasts. For HUASMC, apart from influence of crowders, effect of ascorbic acid supplementations (0 µM, 25 µM, 50 µM and 100 µM) on cell's metabolic activity was also analysed. Briefly, at the end of culture time points, cells were washed with HBSS and then diluted alamarBlue® was added. After 4 hours of incubation at 37° C., absorbance was measured at 550 and 595 nm. Cell viability was expressed in terms of reduction percentage of alamarBlue®.

Results

A. Evaluation of Different Cells to Identify the most Suitable Cell Type for Maximum Collagen Production.

Human lung fibroblasts (WI-38; American tissue culture collection), human dermal fibroblasts (WS-1; American tissue culture collection), and human umbilical arterial smooth muscle cells (huasmc; clonetics, UASMC-human umbilical arterial smooth muscle cells; Lonza cc-2579) were evaluated. Cells from pathophysiologies (eg hypertrophic scar) have not been evaluated since disease transmission may occur. Although we would have expected fibroblasts to produce more collagen, our data indicated that HUASMC deposited higher amounts of collagen-1 when crowded with 100 µg/ml of DxS and 75 µg/ml carrageenan.

B. Evaluation of Different Serum Concentrations to Identify the most Suitable Concentration for Maximum Collagen Production.

To evaluate the optimum serum supply for maximum collagen type I deposition, first we tested 500 kDa dextran sulphate (DxS) (100 µg/ml) as a macromolecular crowder. We identified the 0.5% fetal bovine serum FBS supplementation as the optimal serum concentration for maximum collagen type I deposition. Our data indicate that WI-38 fibroblasts deposited higher extracellular matrix (ECM) in the presence of 500 KDa DxS (100 µg/ml) after 2 days in culture at FBS concentration ranging from 0.5 to 1.0% (p<0.001). Having identified that maximum ECM deposition is achieved by day 2, we tested the influence of various FBS concentrations (0, 0.5, 1.0, 2.0, 5.0 and 10.0%) on the culture of WS1 fibroblasts. Again, we identified the 0.5% to 1% FBS supplementation as the optimal serum concentration for maximum ECM deposition.

C. Evaluation of Different Macromolecules, in Regards to Hydrodynamic Radius, to Identify the most Suitable Hydrodynamic Radius for Maximum Collagen Production.

After we identified the optimal serum concentration (0.5% FBS), we tested other crowding molecules (37.5 mg/ml FICOLL™ 70 and 25 mg/ml FICOLL™ 400 (neutral branched hydrophilic polysaccharides); 100 µg/ml polysodium-4-styrene sulfonate (PSS), 100 µl/ml sepharose-CL and 75 µg/ml carrageenan) cells that are customarily used for tissue engineering applications of lung, skin, lung and blood vessel. Our data indicate that macromolecular crowding significantly increased ECM deposition (p<0.001) and among the macromolecules used, carrageenan induced the highest ECM deposition (p<0.001). Carrageenan enhanced collagen-I deposition up to 20-30 times more within 48 hours.

D. Evaluation of Different Concentrations of Human Serum to Identify the most Suitable Concentration for Maximum Host-Specific Collagen Production.

To eliminate any chance of interspecies disease transmission and xenotransplant rejection; we also tested commercially available human serum as an alternative to FBS. Surprisingly, 0.5% of human serum supply not only worked consistently for macromolecular crowding, it approximately doubled the deposition of collagen type I in comparison to 0.5% FBS supplementation.

E. Evaluation of Deposition of other Extracellular Matrix Molecules.

Apart from collagen type I, the fibronectin deposition was also analysed immunocytochemically to evaluate its pattern of deposition with collagen type I. Immunocytochemistry results further confirmed the enhanced deposition of collagen I and its co-localisation with fibronectin in the presence of macromolecular crowders as shown in the immunocytochemistry figures.

F. Evaluation of Crowders on Cell Morphology and Metabolic Activity.

Cell morphology and viability were analysed using phase contrast microscopy and AlamarBlue® assay respectively at day 2, 4 and 6. Phase contrast microscopy revealed that the fibroblasts maintained their spindle-shaped morphology independent of the macromolecular crowder present or the serum concentration up to 6-days in culture. AlamarBlue® analysis demonstrated that cell metabolic activity was not affected, independent of the macromolecular crowder present or the serum concentration even up to 6-days in culture (p>0.05).

G. Dynamic Light Scattering

The dynamic light scattering analysis demonstrated that the negatively charged macromolecules (carrageenan, dextran sulphate and PSS) had significant higher hydrodynamic diameter (Z-Ave, d.nm) than their neutral counterparts (FICOLL™ 70, FICOLL™ 400 (neutral branched hydrophilic polysaccharides)).

The size dispersion by intensity confirms that the negatively charged macromolecules (carrageenan, dextran sulphate and PSS) are highly polydispersed and among them, carrageenan is the most polydispersed.

Having identified carrageenan as promising new crowding molecule, we evaluated the influence of macromolecular crowding in human umbilical smooth muscle cells in the presence of various concentrations of ascorbic acid (ascorbic acid was used to induce collagen production). Our data indicate the macromolecular crowding significantly increased ECM deposition ($p<0.001$). However, the presence of ascorbic acid did not affected ECM deposition ($p>0.05$).

CONCLUSION

Figure 20:
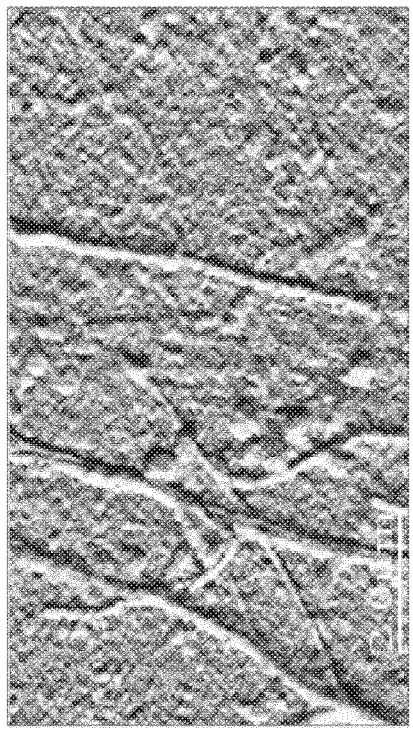
FIG. 20: A structural analysis by atomic force microscopy of the tissue substitute for the invention.
Figure 20:
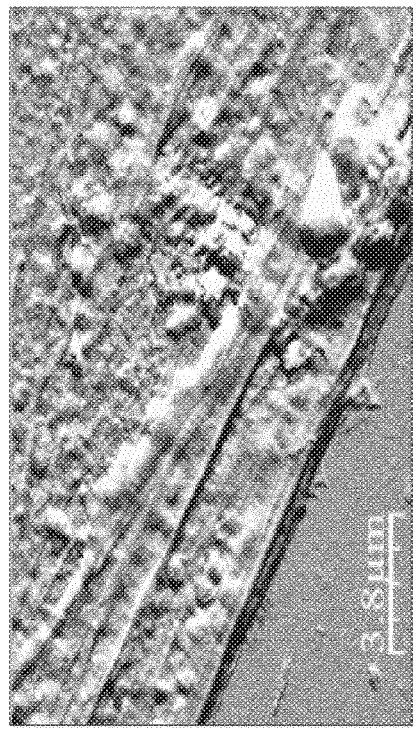
Figure 20:
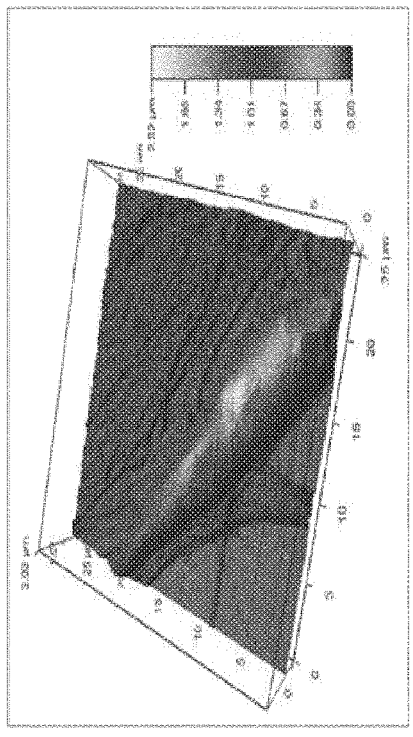
Figure 20:
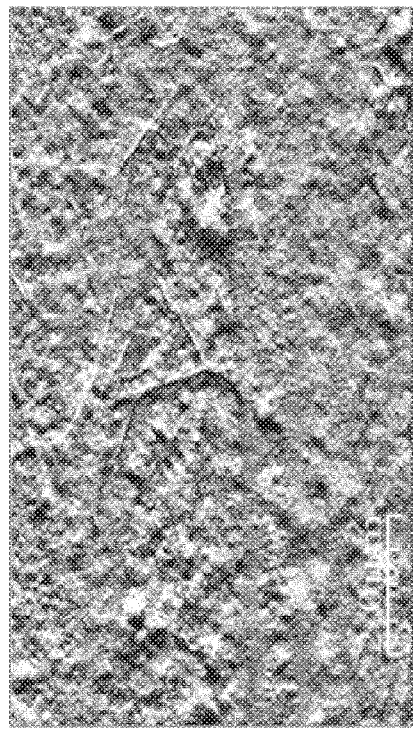

FIG. 20 shows a preliminary structural analysis by atomic microscopy of the human tissue substitute of the invention. Tissue substitute shows a quartered staggered arrangement in which collagen fibres are aligned and similar to those found in native tissue. Thus the tissue matrix or substitute of the invention imitates native tissue.

Thus taking collagen production as a measure of metabolic activity and the stability of the artificial tissue construct, the invention has shown that the growth of cells in a macro molecular crowded environment using highly polydispersed molecules results in an appropriately aligned and functionally metabolising cell layer.

In particular, macromolecular crowding enhances the extracellular matrix (ECM) deposition from human lung, skin, bone and tendin cells. It also enhances ECM deposition even at low serum concentrations. Macromolecular polydispersity ehances ECM deposition. Most importantly, macromolecular crowding des not affect cell morphology, metabolic activity and viability.

The words "comprises/comprising" and the words "having/including" when used herein with reference to the present invention are used to specify the presence of stated features, integers, steps or components but does not preclude the presence or addition of one or more other features, integers, steps, components or groups thereof.

It is appreciated that certain features of the invention, which are, for clarity, described in the context of separate embodiments, may also be provided in combination in a single embodiment. Conversely, various features of the invention which are, for brevity, described in the context of a single embodiment, may also be provided separately or in any suitable sub-combination.

REFERENCES

1. Evans, P., et al., *Cold preserved nerve allografts: changes in basement membrane, viability, immunogenicity, and regeneration*. Muscle Nerve, 1998. 21(11): p. 1507-1522.
2. Willerth, S. M. and S. E. Sakiyama-Elbert, *Approaches to Neural Tissue Engineering Using Scaffolds for Drug Delivery*. Adv Drug Deliv Rev, 2007. 59(4-5): p. 325-338.
3. Den Dunnen, W., et al., *A new PLLA/PCL copolymer for nerve regeneration*. J Mater Sci: Mater Med, 1993. 4: p. 521-525.
4. Madison, R., et al., *Increased rate of peripheral nerve regeneration using bioresorbable nerve guides and a laminin-containing gel*. Exp Neurol, 1985. 88(3): p. 767-772.
5. Evans, G., et al., *In vivo evaluation of poly(l-lactic acid) porous conduits for peripheral nerve regeneration*. Biomaterials, 1999. 20(12): p. 1109-1115.
6. Evans, G. R., et al., *Bioactive poly(L-lactic acid) conduits seeded with Schwann cells for peripheral nerve regeneration*. Biomaterials, 2002. 23(3): p. 841-8.
7. Chew, S. Y., et al., *Aligned Protein-Polymer Composite Fibers Enhance Nerve Regeneration: A Potential Tissue-Engineering Platform*. Adv Funct Mater, 2007. 17(8): p. 1288-1296.
8. Kim, Y.-t., et al., *The role of aligned polymer fiber-based constructs in the bridging of long peripheral nerve gaps*. Biomaterials, 2008. 29: p. 3117-3127.
9. Li, X.-k., et al., *Characteristics of PLGA-gelatin complex as potential artificial nerve scaffold*. Colloids and Surfaces B: Biointerfaces, 2007. 57(2): p. 198-203.
10. Harley, B. A., et al., *Fabricating tubular scaffolds with a radial pore size gradient by a spinning technique*. Biomaterials, 2006. 27(6): p. 866-874.
15. Archibald, S., et al., *Monkey median nerve repaired by nerve graft or collagen nerve guide tube*. J Neurosci: Part 2, 1995. 15(5): p. 4109-4123.
16. Colin, W. and R. Donoff, *Nerve regeneration through collagen tubes*. J Dent Res, 1984. 63(7): p. 987-993.
17. Itoh, S., et al., *Evaluation of cross-linking procedures of collagen tubes used in peripheral nerve repair*. Biomaterials, 2002. 23(23): p. 4475-4481.
18. Ahmed, M. R., et al., *Microwave irradiated collagen tubes as a better matrix for peripheral nerve regeneration*. Brain Research, 2005. 1046(1-2): p. 55-67.
19. Chen, P.-R., et al., *Biocompatibility of NGF-grafted GTG membranes for peripheral nerve repair using cultured Schwann cells*. Biomaterials, 2004. 25(25): p. 5667-5673.
20. Chen, Y.-S., et al., *An in vivo evaluation of a biodegradable genipin-cross-linked gelatin peripheral nerve guide conduit material*. Biomaterials, 2005. 26(18): p. 3911-3918.
21. Ju, Y.-E., et al., *Enhanced Neurite Growth from Mammalian Neurons in Three-Dimensional Salmon Fibrin Gels*. Biomaterials, 2007. 28(12): p. 2097-2108.
    1. Harve K, Vigneshwar R, Rajagopalan R, Raghunath M. Macromolecular crowding in vitro as means of emulating cellular interiors: when less might be more. PNAS 2008; 105(51):119.
    2. Lareu R R, Arsianti I, Subramhanya H K, Yanxian P, Raghunath M. In Vitro Enhancement of Collagen Matrix Formation and Crosslinking for Applications in Tissue Engineering: A Preliminary Study. Tissue Engineering 2007; 13(2):385-391.
    3. Lareu R R, Subramhanya K H, Peng Y, Benny P, Chen C, Wang Z, Rajagopalan R, Raghunath M. Collagen matrix deposition is dramatically enhanced in vitro when crowded with charged macromolecules: The biological relevance of the excluded volume effect. FEBS Letters 2007; 581:2709-2714.
    4. Lareu R, Harve K, Raghunath M. Emulating a crowded intracellular environment in vitro dramatically improves RT-PCR performance. Biochem Biophys Res Commun 2007; 363(1):171-177.

The invention claimed is:

1. A method for production of a tissue substitute, comprising:
    adding a culture medium comprising a plurality of large polydispersed particulate carrageenan macromolecular crowders to animal cells in a culture.

2. The method as claimed in claim 1, further comprising a plurality of second macromolecular crowders, wherein the animal cells are cultured in the presence of both the plurality of large polydispersed particulate carrageenan macromolecular crowders and the plurality of second macromolecular crowders wherein the plurality of second macromolecular crowders are large poly-dispersed macromolecules.

3. The method as claimed in claim 2, wherein the polydispersed particulate carrageenan macromolecular crowders and the second macromolecular crowders are neutral or negatively charged.

4. The method as claimed in claim 2, wherein the second macromolecular crowders are selected from the group consisting of dextrans, dextran sulphate, bovine serum albumin, sodium alginate, polyethylene glycol, sepharose-CL and polysodium-4-styrene sulfonate.

5. The method as claimed in claim 1, wherein the animal cells are selected from the group consisting of lung fibroblasts, dermal fibroblasts, skin fibroblasts, human tenocytes, normal human osteoblasts and human umbilical artery smooth muscle cells.

6. The method as claimed in claim 1, wherein the animal cells are human umbilical artery smooth muscle cells.

7. The method as claimed in claim 1, wherein the animal cells are cultured in the presence of culture medium supplemented with fetal bovine serum, human serum, ascorbic acid phosphate, or a combination thereof.

8. The method as claimed in claim 7, wherein the animal cells are supplemented with human serum.

9. The method as claimed in claim 8, when the human serum is used at 0.5% to 1% volume to volume.

10. The method of claim 1, wherein the animal cells are animal cells that can form a tissue.

* * * * *